(12) United States Patent
Katz et al.

(10) Patent No.: US 10,854,319 B2
(45) Date of Patent: Dec. 1, 2020

(54) SYSTEMS AND METHODS FOR VISUALIZING CLINICAL TRIAL SITE PERFORMANCE

(71) Applicant: Analgesic Solutions, Wayland, MA (US)

(72) Inventors: Nathaniel P. Katz, Natick, MA (US); Arturo J. Morales, Stow, MA (US)

(73) Assignee: Analgesic Solutions LLC, Wayland, MA (US)

( * ) Notice: Subject to any disclaimer, the term of this patent is extended or adjusted under 35 U.S.C. 154(b) by 0 days.

(21) Appl. No.: 16/680,898

(22) Filed: Nov. 12, 2019

(65) Prior Publication Data

US 2020/0082920 A1    Mar. 12, 2020

Related U.S. Application Data

(63) Continuation of application No. PCT/US2018/031829, filed on May 9, 2018.

(60) Provisional application No. 62/503,537, filed on May 9, 2017.

(51) Int. Cl.
| | | |
|---|---|---|
| G16H 10/20 | (2018.01) | |
| G06T 11/00 | (2006.01) | |
| G06T 11/60 | (2006.01) | |
| G16H 40/67 | (2018.01) | |
| A61B 5/00 | (2006.01) | |

(52) U.S. Cl.
CPC ........ *G16H 10/20* (2018.01); *G06T 11/001* (2013.01); *G06T 11/60* (2013.01); *A61B 5/4848* (2013.01); *A61B 5/742* (2013.01); *G16H 40/67* (2018.01)

(58) Field of Classification Search
CPC ...... G16H 10/20; G16H 40/67; G06T 11/001; G06T 11/60; A61B 5/4848; A61B 5/742
See application file for complete search history.

(56) References Cited

U.S. PATENT DOCUMENTS

| | | | | |
|---|---|---|---|---|
| 8,706,537 | B1 * | 4/2014 | Young | G06F 19/3418 705/7.11 |
| 2006/0253045 | A1 * | 11/2006 | Coifman | A61B 5/0871 600/538 |
| 2011/0082827 | A1 * | 4/2011 | Shiffman | G06N 5/025 706/47 |
| 2011/0282692 | A1 * | 11/2011 | Kane | G06Q 10/06393 705/3 |
| 2012/0053995 | A1 * | 3/2012 | D'Albis | G06Q 10/06393 705/7.39 |
| 2013/0060599 | A1 * | 3/2013 | Jinfeng | G06Q 30/0201 705/7.28 |
| 2013/0311196 | A1 * | 11/2013 | Fay | G06Q 10/0635 705/2 |
| 2014/0232263 | A1 | 8/2014 | Nguyen et al. | |
| 2014/0375650 | A1 | 12/2014 | Grundstrom et al. | |
| 2015/0248843 | A1 * | 9/2015 | Katz | A61B 5/0053 434/236 |

OTHER PUBLICATIONS

International Search Report dated Aug. 2, 2018 for International Patent Application No. PCT/US2018/031829, 3 pages.

* cited by examiner

*Primary Examiner* — Abderrahim Merouan
(74) *Attorney, Agent, or Firm* — Morgan, Lewis & Bockius LLP

(57) ABSTRACT

Systems and methods for visualizing clinical trial site performance, or other multi-dimensional (or multi-parameter) datasets.

16 Claims, 14 Drawing Sheets

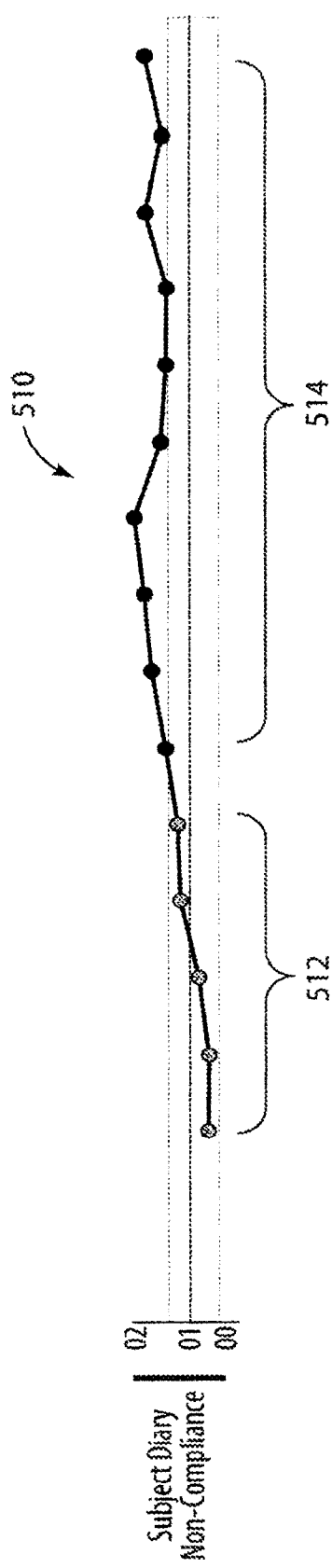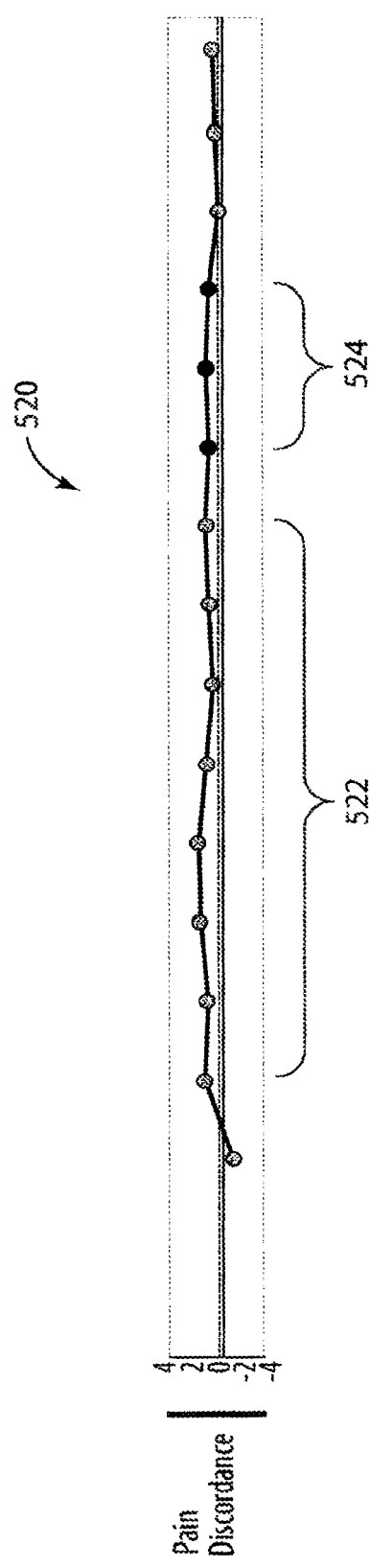
FIG. 5A
FIG. 5B

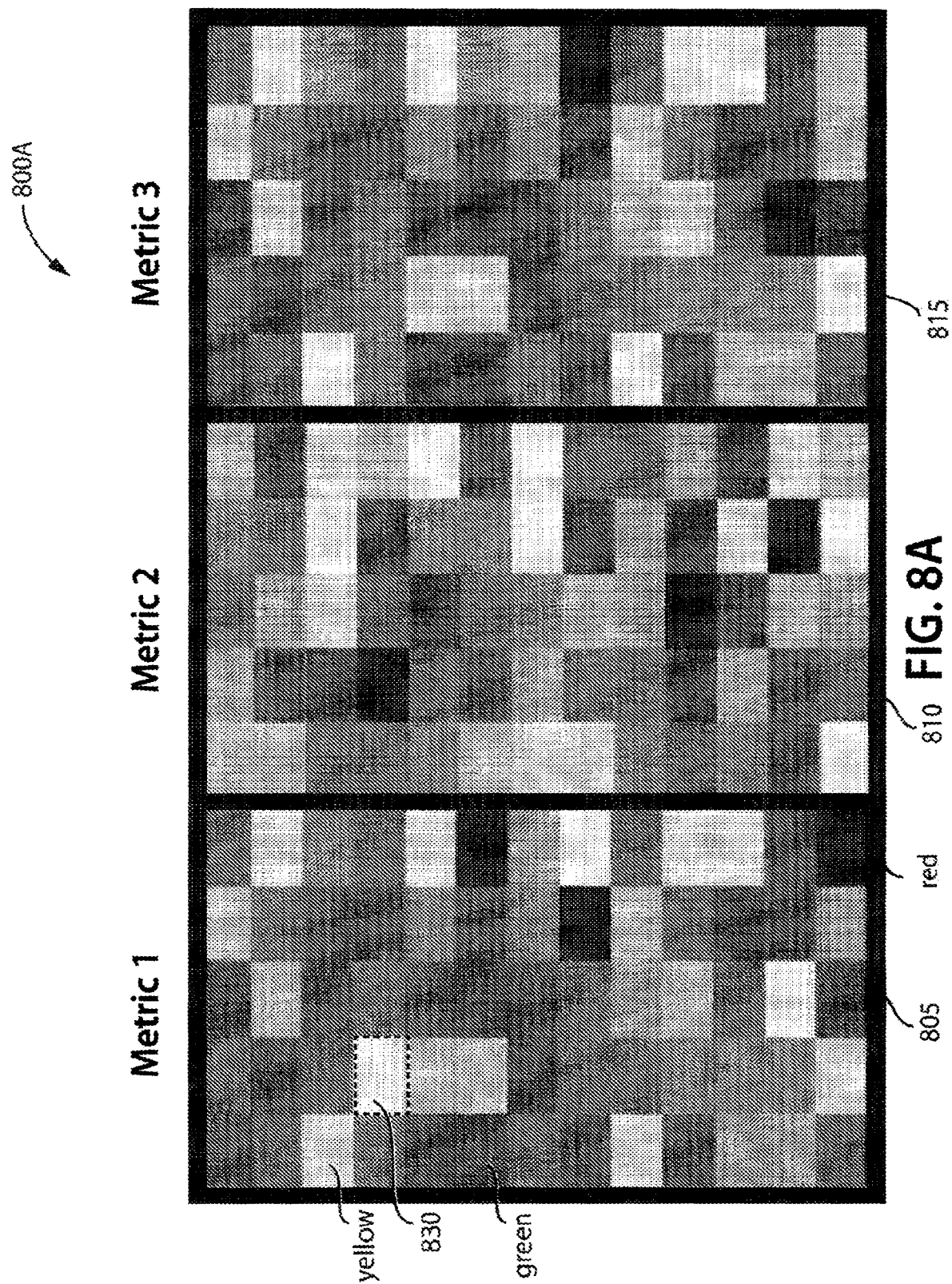

SYSTEMS AND METHODS FOR VISUALIZING CLINICAL TRIAL SITE PERFORMANCE

STATEMENT OF RELATED APPLICATIONS

This application is a continuation application of International Patent Application No. PCT/US2018/031829, filed May 9, 2018, which claims priority to U.S. Provisional Application No. 62/503,537, filed May 9, 2017, both of which are herein incorporated by reference in their entireties.

BACKGROUND

Many clinical trials fail to distinguish efficacy of a known active drug (e.g., an analgesic) from placebo. Variability of study results among different trial sites is a factor in such failures. While trial sites may be individually monitored during a study, monitoring efforts typically focus on data completeness and regulatory compliance rather than factors associated with assay sensitivity. As a result, site failure (e.g., a site's inability to show a benefit of a proposed drug over placebo, particularly when compared to other sites in the same trial) may be discovered only after the trial is complete and the trial database is locked. At that point, intervention is no longer be possible.

BRIEF DESCRIPTION OF DRAWINGS

FIGS. 5A-5B show illustrative control charts generated by applying statistical process control (SPC) techniques to clinical trial data, in accordance with some embodiments.

FIGS. 8A-8D show illustrative visual representations 800A-800D, each having illustrative regions corresponding, respectively, to three different quality metrics for a trial site, in accordance with some embodiments.

SUMMARY

Figure 1:
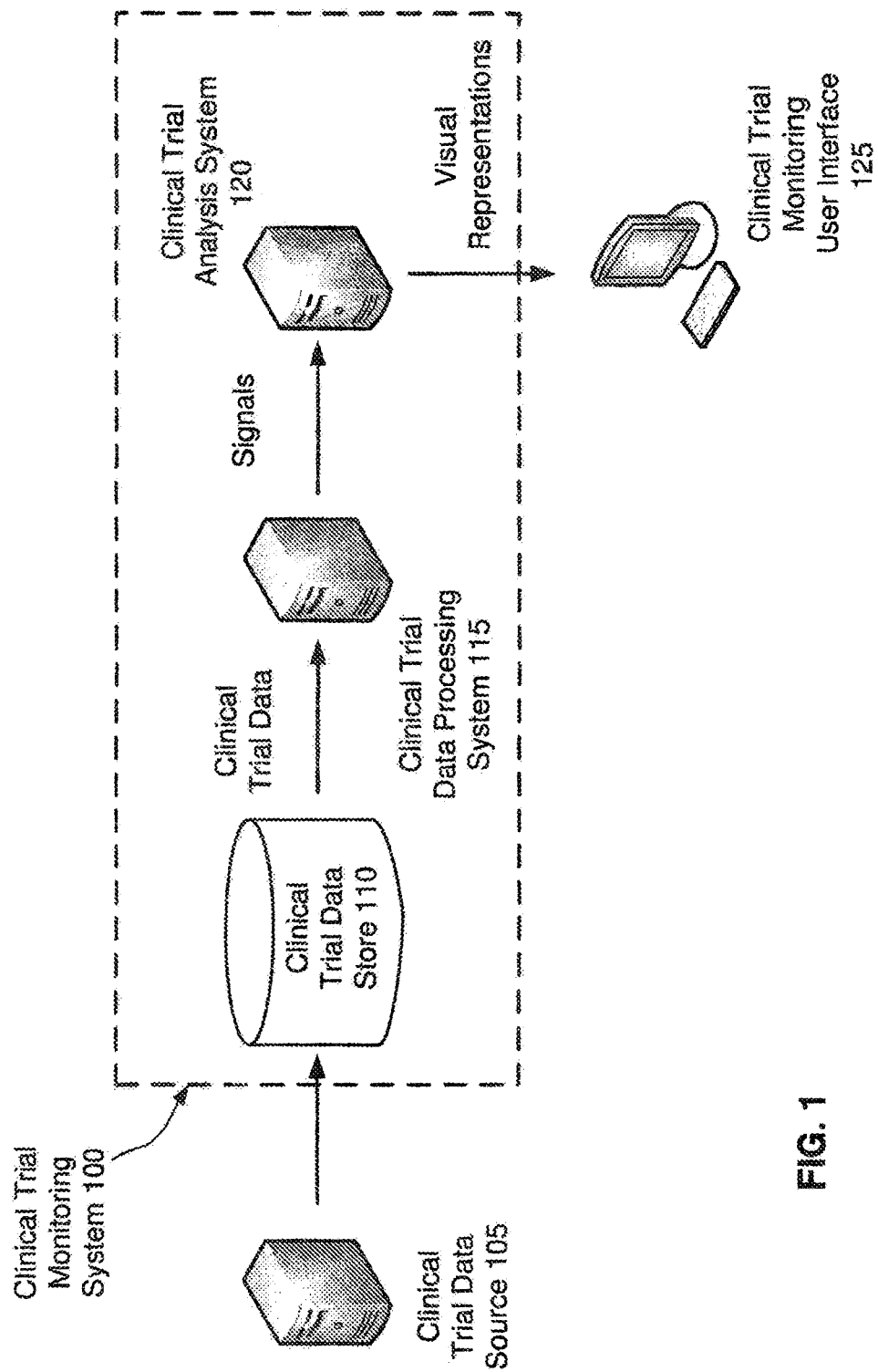
FIG. 1 shows an illustrative clinical trial monitoring system 100, in accordance with some embodiments.

Provided herein, inter alia, are systems and methods for representation of multi-parameter datasets (also referred to herein as multi-dimensional datasets). Such representations may be themselves two dimensional but may comprise and thus relay information about three, four, five, or more parameters (and thus they may be two-dimensional renderings of multi-dimensional datasets). The datasets may be related to clinical trials, but are not so limited. One of ordinary skill will appreciate based on this disclosure that other datasets may be manipulated and thus represented as described herein. Thus, while for convenience and brevity this disclosure highlights clinical trial data, it is to be understood that other datasets may similarly be used as described herein. Such datasets may include virtually any quantifiable parameter, such as but not limited to size, time (e.g., as in a particular date, or a particular period of time, or a particular day of the week, or a particular month, or a particular year), time period or duration of time, location (e.g., city, state, country, continent), frequency or magnitude or severity of an event, etc.

In one aspect, this disclosure provides a visual representation based on clinical trial data, the visual representation comprising:

a plurality of regions, each region of the plurality of regions corresponding to a respective trial site of a plurality of trial sites participating in a clinical trial, wherein, for at least one region of the plurality of regions:

the at least one region of the plurality of regions comprises a plurality of sub-regions, each sub-region of the plurality of sub-regions corresponding to a respective time interval of a plurality of time intervals;

for each sub-region of the plurality of sub-regions, a size of the sub-region is indicative of a number of human subjects who were active at the trial site corresponding to the at least one region during the time interval corresponding to the sub-region; and for each sub-region of the plurality of sub-regions, a visual indication is provided based on a quality score for the trial site corresponding to the at least one region and the time interval corresponding to the sub-region, wherein the quality score is based on at least one trial site quality metric, and on data collected from the human subjects who were active at that trial site during that time interval.

In another aspect, this disclosure provides a visual representation comprising:

a plurality of regions, each region of the plurality of regions corresponding to a respective first value of a plurality of first values for a first parameter, wherein, for at least one region of the plurality of regions:

the at least one region of the plurality of regions comprises a plurality of sub-regions, each sub-region of the plurality of sub-regions corresponding to a respective second value of a plurality of second values for a second parameter different from the first parameter;

for each sub-region of the plurality of sub-regions, a size of the sub-region is indicative of a third value based on a data set associated with the first value corresponding to the at least one region and the second value corresponding to the sub-region; and for each sub-region of the plurality of sub-regions, a visual indication is provided based on a fourth value for the first value corresponding to the at least one region and the second value corresponding to the sub-region, wherein the fourth value is related to the third value.

In another aspect, a method for visualizing clinical trial site performance, comprising acts of:

obtaining data relating to a plurality of trial sites participating in a clinical trial, the data comprising, for each trial site of the plurality of trial sites:

trial site activity data indicating, for each time interval of a plurality of time intervals, a number of human subjects who were active at the trial site during that time interval; and trial site quality data indicating, for each time interval of the plurality of time intervals, a quality score according to at least one trial site quality metric, wherein the quality score is based on data collected from the human subjects who were active at the trial site during that time interval; and providing at least one visual representation, wherein the visual representation comprises a plurality of regions, each region of the plurality of regions corresponding to a respective trial site of the plurality of trial sites, and wherein, for at least one region of the plurality of regions:

the at least one region of the plurality of regions comprises a plurality of sub-regions, each sub-region of the plurality of sub-regions corresponding to a respective time interval of the plurality of time intervals;

for each sub-region of the plurality of sub-regions, a size of the sub-region is indicative of the number of human subjects who were active at the trial site corresponding to the at least one region during the time interval corresponding to the sub-region; and for each sub-region of the plurality of sub-regions, a visual indication is provided based on the quality score for the trial site corresponding to the at least one region and the time interval corresponding to the sub-region.

In some embodiments, the method further comprises an act of recommending an intervention to address a quality issue at a trial site.

In some embodiments, the method further comprises the clinical trial is an on-going clinical trial, and wherein the method further comprises an act of recommending removal of a trial site from the on-going clinical trial or a future clinical trial due to a quality issue.

In another aspect, the disclosure provides a system for visualizing clinical trial site performance, comprising:

at least one non-transitory computer-readable medium storing executable instructions; and at least one processor programmed by the executable instructions to:

access data relating to a plurality of trial sites participating in a clinical trial, the data comprising, for each trial site of the plurality of trial sites:

trial site activity data indicating, for each time interval of a plurality of time intervals, a number of human subjects who were active at the trial site during that time interval; and trial site quality data indicating, for each time interval of the plurality of time intervals, a quality score according to at least one trial site quality metric, wherein the quality score is based on data collected from the human subjects who were active at that trial site during that time interval; and cause at least one visual representation of the data to be rendered on at least one display, wherein the at least one visual representation comprises a plurality of regions, each region of the plurality of regions corresponding to a respective trial site of the plurality of trial sites, and wherein, for at least one region of the plurality of regions:

the at least one region of the plurality of regions comprises a plurality of sub-regions, each sub-region of the plurality of sub-regions corresponding to a respective time interval of the plurality of time intervals;

for each sub-region of the plurality of sub-regions, a size of the sub-region is indicative of the number of human subjects who were active at the trial site corresponding to the at least one region during the time interval corresponding to the sub-region; and for each sub-region of the plurality of sub-regions, a visual indication is provided based on the quality score for the trial site corresponding to the at least one region and the time interval corresponding to the sub-region.

In some embodiments, for at least one sub-region of the plurality of sub-regions, the visual indication comprises a color selected based on the quality score. In some embodiments, the at least one processor is programmed to: select the color at least in part by comparing the quality score to at least one threshold.

In some embodiments, the visual indication further comprises a color intensity selected based on the quality score.

In some embodiments, for at least one sub-region of the plurality of sub-regions, the visual indication comprises a fill pattern selected based on the quality score. In some embodiments, the at least one processor is programmed to: select the fill pattern at least in part by comparing the quality score to at least one threshold.

In some embodiments, the visual indication further comprises a fill pattern density selected based on the quality score.

In some embodiments, the at least one processor is programmed to: cause the plurality of regions to be arranged based on geographic locations of the corresponding trial sites.

In some embodiments, the at least one processor is programmed to: cause the plurality of sub-regions of the at least one region to be arranged chronologically based on the corresponding time intervals.

In some embodiments, for each trial site of the plurality of trial sites and each time interval of the plurality of time intervals, the quality score for that trial site and that time interval is based on a number of abnormal events observed at the trial site during that time interval.

In another aspect, the disclosure provides a system for visualizing clinical trial site performance, comprising:

at least one non-transitory computer-readable medium storing executable instructions; and at least one processor programmed by the executable instructions to:

access data relating to a trial site participating in a clinical trial, the data comprising:

trial site activity data indicating, for each time interval of a plurality of time intervals, a number of human subjects who were active at the trial site during that time interval; and trial site quality data indicating, for each time interval of the plurality of time intervals, a plurality of quality scores associated with a plurality of trial site quality metrics respectively, wherein at least one quality score of the plurality of quality scores is based on data collected from the human subjects who were active at that trial site during that time interval; and cause at least one visual representation of the data to be rendered on at least one display, wherein the at least one visual representation comprises a plurality of regions, each region of the plurality of regions corresponding to a respective trial site quality metric of the plurality of trial site quality metrics, and wherein, for at least one region of the plurality of regions:

the at least one region of the plurality of regions comprises a plurality of sub-regions, each sub-region of the plurality of sub-regions corresponding to a respective time interval of the plurality of time intervals; and for each sub-region of the plurality of sub-regions, a visual indication is provided based on the respective quality score for the trial site quality metric corresponding to the at least one region and the time interval corresponding to the sub-region.

In some embodiments, for at least one sub-region of the plurality of sub-regions, the visual indication comprises a color selected based on the respective quality score. In some embodiments, the at least one processor is programmed to: select the color at least in part by comparing the quality score to at least one threshold.

In some embodiments, the visual indication further comprises a color intensity selected based on the quality score.

In some embodiments, for at least one sub-region of the plurality of sub-regions, the visual indication comprises a fill pattern selected based on the respective quality score. In some embodiments, the at least one processor is programmed to: select the fill pattern at least in part by comparing the quality score to at least one threshold.

In some embodiments, the visual indication further comprises a fill pattern density selected based on the quality score.

In some embodiments, at least one trial site quality metric of the plurality of trial site quality metrics comprises a multivariate metric.

In some embodiments, for each time interval of the plurality of time intervals, the quality score for that time interval is based on a number of abnormal events observed at the trial site during that time interval.

In some embodiments, the at least one processor is further programmed to: recommend an intervention to address a quality issue at the trial site In some embodiments, the clinical trial is an on-going clinical trial, and wherein the at least one processor is further programmed to: recommend removal of the trial site from the on-going clinical trial or a future clinical trial due to a quality issue.

In another aspect, this disclosure provides a system for visualizing clinical trial site performance, comprising:

at least one non-transitory computer-readable medium storing executable instructions; and at least one processor programmed by the executable instructions to:

access data relating to a plurality of trial sites participating in a clinical trial, the data comprising, for each trial site of the plurality of trial sites:

subject status data indicating, for each subject of a plurality of subjects associated with the trial site, a status of the subject within the clinical trial;

cause at least one visual representation of the data to be rendered on at least one display, wherein the at least one visual representation comprises a plurality of regions, each region of the plurality of regions corresponding to a respective trial site of the plurality of trial sites, and wherein, for at least one region of the plurality of regions:

the at least one region of the plurality of regions comprises a plurality of indicia, each indicium of the plurality of indicia corresponding to a respective subject of the plurality of subjects; and for each indicium of the plurality of indicia, a visual indication is provided based on the status of the subject within the clinical trial.

In some embodiments, for at least one indicium of the plurality of indicia, the visual indication comprises a color selected based on the status of the subject.

In some embodiments, the visual indication further comprises a color intensity selected based on the status of the subject.

In some embodiments, for at least one indicium of the plurality of indicia, the visual indication comprises a fill pattern selected based on the status of the subject.

In some embodiments, the visual indication further comprises a fill pattern density selected based on the status of the subject.

In some embodiments, the at least one processor is programmed to: cause the plurality of regions to be arranged based on geographic locations of the corresponding trial sites.

Further provided herein is a method performed by any of the foregoing systems, for example, wherein the method is performed prior to completion of the clinical trial. That is, the methods and systems provided herein, at least in the context of a clinical trial, may be used and/or implemented prior to the completion of the trial and thus the data may not be the final data from such trial but rather intermediate data. The ability to monitor and visualize datasets while an analysis, such as a clinical trial, is ongoing allows an end user to modify or manipulate or leave as is one or more aspects of the analysis, such as a clinical site in a clinical trial.

These and other aspects and embodiments will be described in greater detail herein.

DETAILED DESCRIPTION

The inventors have recognized and appreciated that failures of multicenter clinical trials (e.g., Phase 3 clinical trials) are often due to reduced assay sensitivity (i.e., inability of a trial to statistically discriminate an effect of an active drug from that of a placebo). Although a variety of factors may impact assay sensitivity, an important factor may be variability in study conduct between sites in multicenter studies, which introduces "noise" in overall data. For instance, when analyzing data collected at multicenter trials, it is not uncommon to find between-site differences in calculated effect sizes. Such differences may arise because some sites may follow study protocol rigorously, while other sites may do so more haphazardly, thereby degrading effect size.

The inventors have recognized and appreciated that aberrant data patterns resulting from variability in study conduct between sites are rarely detected using current clinical trial monitoring methods, or are detected too late (e.g., after a trial database has been locked). For instance, human monitors may visit clinical trial sites every few months during a study and look for gross violations of data quality (e.g., missing data, mismatches between source documents and case report forms, protocol or good clinical practice violations, etc.). These human monitors may have no therapeutic expertise, and may not analyze data patterns substantively.

Accordingly, in some embodiments, a clinical trial monitoring system may be provided to monitor clinical trial data in near real time, for example, to detect and remedy problems early in clinical trials. For instance, the clinical trial monitoring system may use centralized monitoring techniques to detect data anomalies such as fraud, fabrication, and other non-random distributions.

In some embodiments, a clinical monitoring system may be programmed to perform statistical assessments to timely identify clinical sites where additional training and/or monitoring may be appropriate. For instance, the clinical trial monitoring system may be programmed to identify trial sites with characteristics associated with poor performance or noncompliance. Examples of such characteristics include, but are not limited to, errors in data collection and/or reporting (e.g., missing data, inconsistent data, data outliers, etc.), and/or poor performance with respect to certain metrics (e.g., high screen failure and/or withdrawal rates, high frequency of eligibility violations, delays in reporting data, etc.). In some embodiments, the clinical trial monitoring system may be programmed to identify data trends by examining range, consistency, and/or unusual distribution of data within a site and/or between sites. Such data trends may not be readily detectable by current onsite monitoring techniques.

The inventors have recognized and appreciated that early detection of aberrant data patterns predictive of site failure may allow remediation of a failing site as soon as a problem is detected. Examples of corrective actions include, but are not limited to, retraining site staff on certain aspects related to an observed aberrant data pattern, retraining patients to report symptoms (e.g., pain) accurately, changing study procedure, and closing the failing sites. In some embodiments, a change may be implemented that is consistent with an existing protocol, so that data already collected may not be invalidated.

The inventors have further recognized and appreciated that a large amount of clinical trial data may be collected, which may involve a large number of human subjects participating via many different trial sites over a long period of time. Accordingly, in some embodiments, techniques are provided for visualizing clinical trial data in a concise and intuitive manner. Such visualization techniques may facilitate timely determination as to whether intervention may be appropriate for an on-going clinical trial. Additionally, or alternatively, such visualization techniques may facilitate identification of trial sites with persistent quality issues over multiple clinical trials, which may lead to a recommendation that certain corrective actions be taken, such as additional staff training.

FIG. 1 shows an illustrative clinical trial monitoring system 100, in accordance with some embodiments. In this example, the clinical trial monitoring system 100 may receive clinical trial data from one or more sources, such as clinical trial data source 105. For instance, in some embodiments, the clinical trial data source 105 may be provided by a contract research organization that conducts a clinical trial on behalf of a sponsor (e.g., a pharmaceutical, biotechnology, or medical device company). The clinical trial data source 105 may aggregate data from different trial sites and transmit the data to the clinical trial monitoring system 100.

In some embodiments, clinical trial data received by the clinical trial monitoring system 100 may be stored in a clinical trial data store 110. The clinical trial monitoring system 100 may include a clinical trial data processing system 115 that is programmed to access data from the clinical trial data store 110 and generate one or more signals. In some embodiments, the clinical trial data processing system 115 may be programmed to generate the one or more signals by applying one or more statistical process control (SPC) tests to the data.

As a non-limiting example, the clinical trial data store 110 may store data indicating when each subject visited or otherwise interacted with a trial site and diary entries submitted by the subject as instructed according to a study protocol. The clinical trial data processing system 115 may use this data to calculate, for each subject, a percentage of diary entries that are actually filled, out of all diary entries that the subject is expected to fill, to track one or more endpoints of interest (e.g., a certain type of pain). Such a percentage may be output as a subject-level signal.

Additionally, or alternatively, the clinical trial data processing system 115 may generate a site-level signal, for example, by calculating a diary compliance percentage for each subject who visited or otherwise interacted with a trial site during a certain period of time (e.g., one week, two weeks, three weeks, one month, etc.), and then averaging over all such subjects.

In the example shown in FIG. 1, one or more signals generated by the clinical trial data processing system 115 may be consumed by a clinical trial analysis system 120. In some embodiments, the clinical trial analysis system 120 may include a rules engine programmed to apply one or more rules to one or more signals generated by the clinical trial data processing system 115. As a non-limiting example, the clinical trial analysis system 120 may apply a diary compliance rule to a diary compliance signal. For instance, a diary compliance rule may be triggered if a trial site's diary compliance average is below a selected threshold (e.g., 85%). Additionally, or alternatively, a diary compliance rule may be triggered if, for a certain period of time (e.g., a certain number of consecutive weeks), a trial site's diary compliance average stays below a diary compliance average across all trial sites.

In some embodiments, one or more results produced by the clinical trial analysis system 120 may be presented to a user via a clinical trial monitoring user interface 125. In some embodiments, the clinical trial monitoring user interface 125 may be a web interface, and one or more visual representations of analysis results may be rendered by a web browser running on the user's computer. However, that is not required, as in some embodiments an application (other than a web browser) may be installed on the user's computer, and may be programmed to present one or more visual representations of results produced by the clinical trial analysis system 120.

Although various details of implementation are shown in FIG. 1 and discussed above, it should be appreciated that aspects of the present disclosure are not limited to the use of any particular component, or combination of components, or to any particular arrangement of components. Furthermore, each component may be implemented in any suitable manner, such as using one or more parallel processors operating at a same location or different locations.

Figure 2:
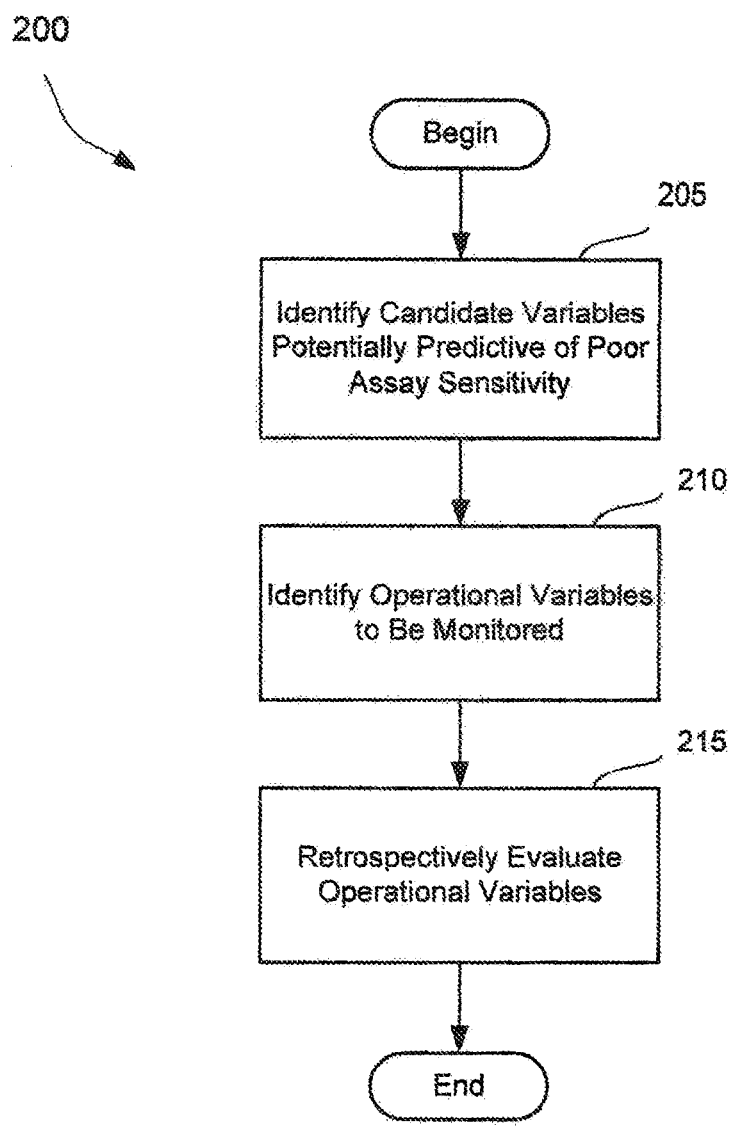
FIG. 2 shows an illustrative process 200 for determining one or more variables predictive of poor assay sensitivity, in accordance with some embodiments.

FIG. 2 shows an illustrative process 200 for determining one or more variables predictive of poor assay sensitivity, in accordance with some embodiments. For instance, the process 200 may be used to determine one or more variables to be monitored by the illustrative clinical trial monitoring system 100 shown in FIG. 1.

At act 205, one or more candidate variables may be identified that are potentially predictive of site failure in clinical trials. As an example, a candidate variable may pertain to a certain subject (e.g., diary compliance for that subject). As another example, a candidate variable may pertain to a certain trial site (e.g., average diary compliance across all subjects enrolled at the trial site). As yet another example, a candidate variable may pertain to multiple trial sites (e.g., average diary compliance across all subjects enrolled at all trial sites in a geographical region). Any one or more subject-level, site-level, multi-site, and/or other types of variables may be identified, as aspects of the present disclosure are not limited to the use of any particular type of variables.

In some embodiments, one or more candidate variables may be identified based on input from domain experts. For instance, in some embodiments, one or more experts in a certain type of clinical trials (e.g., analgesic trials) may propose candidate variables based on the experts' knowledge of various factors associated with site performance. Examples of suitable experts include, but are not limited to, clinicians, statisticians, data managers, and project managers.

In some embodiments, one or more candidate variables may be automatically identified based on a study protocol. For instance, in some embodiments, a study protocol may be searched to identify one or more variables known to affect site performance, and an identified variable may be automatically mapped to data in the clinical trial data store 110 that is relevant for evaluating the variable.

As a non-limiting example, Table 1 below shows an illustrative list of candidate variables that are potentially predictive of site failure in analgesic trials. It should be appreciated that aspects of the present disclosure are not limited to the use of any of these candidate variables, as other candidate variables may also be suitable. Moreover, one or more of the techniques disclosed herein may be used to monitor clinical trials other than analgesic trials.

TABLE 1

Examples of potential predictors of poor assay sensitivity

| Clinical Trial Parameter | Static vs. Dynamic | Availability | Predictive Value | Selected for Evaluation? |
|---|---|---|---|---|
| *Site Profile* | | | | |
| Unique site identifier | Static | Yes | N/A | No |
| Location (city, state, country, region) | Static | Yes | N/A | No |
| Clinical practice or research only | Static | Difficult | N/A | No |
| Number of previous trials in therapeutic area | Static | Difficult | N/A | No |
| Years of experience in therapeutic area | Static | Difficult | N/A | No |
| *Principal Investigator (PI)* | | | | |
| Specialty | Static | Difficult | N/A | No |
| Years of experience in therapeutic area research | Static | Difficult | N/A | No |
| Number of previous studies in therapeutic area | Static | Difficult | N/A | No |
| Investigator demographics | Static | Yes | N/A | No |
| Currently practicing | Static | Difficult | N/A | No |
| Turnover of PI at a site | Dynamic | Difficult | Medium | No |
| Quantity of Publications | Static | Yes | N/A | No |
| Previous experience with drug (e.g., particular drug, or class of drugs) | Static | Difficult | N/A | No |
| *Study Coordinators* | | | | |
| How many participated in study | Dynamic | Difficult | N/A | No |
| Turnover | Dynamic | No | N/A | No |
| Years of experience in therapeutic area research | Static | No | N/A | No |
| Number of previous therapeutic area studies | Static | No | N/A | No |
| Coordinator demographics | Static | No | N/A | No |
| *Site-Level Performance Metrics* | | | | |
| Date of site initiation (compared to other sites) | Static | Difficult | N/A | No |
| Number of patients screened/enrolled/randomized | Dynamic | Yes | Medium | No |
| Recruitment rate (patients/month) | Dynamic | Yes | High | No |
| Number of protocol violations (PVs) (total and per subject) | Dynamic | Difficult | N/A | No |
| Screen fail rate | Dynamic | Yes | Medium | No |
| Screen fail reason | Dynamic | Yes | Low | No |
| Outreach methods | Dynamic | No | N/A | No |
| Number of subjects recruited for each outreach method | Dynamic | No | N/A | No |
| Number of queries per subject | Dynamic | Difficult | N/A | No |
| Median time to query response | Dynamic | Difficult | N/A | No |
| Audit findings | Dynamic | Difficult | N/A | No |
| Median time to data entry | Dynamic | Yes | Medium | No |
| *Subject-Level Clinical Trial Data (aggregated at site level)* | | | | |
| Subject Demographics | Dynamic | Yes | Low | No |
| Primary language | Dynamic | Difficult | N/A | No |
| Enrollment order (compared to other subjects) | Dynamic | Yes | Low | No |
| Missing pre-randomization data | Dynamic | Yes | Medium | No |
| Missing post-randomization data | Dynamic | Yes | Medium | No |

TABLE 1-continued

Examples of potential predictors of poor assay sensitivity

| Clinical Trial Parameter | Static vs. Dynamic | Availability | Predictive Value | Selected for Evaluation? |
|---|---|---|---|---|
| Average pre-randomization primary endpoint score | Dynamic | Yes | Medium | No |
| Change in pain score over time | Dynamic | Yes | Medium | No |
| Variability in pain score over time | Dynamic | Yes | Medium | No |
| Variability in post-randomization primary endpoint scores; change in variability in pain scores over time | Dynamic | Yes | Medium | No |
| Discordance between different measures of same concept such as pain (e.g., PI NRS (Pain Intensity - Numerical Rating Scale) vs. WOMAC (Western Ontario and McMaster Universities Osteoarthritis Index) pain) | Dynamic | Yes | High | Yes |
| Number of adverse events (AEs)/serious adverse events (SAEs) (total, %) | Dynamic | Yes | Medium | No |
| Dropouts (total, %) | Dynamic | Yes | Medium | No |
| Baseline composite disease severity (total WOMAC score) | Dynamic | Yes | Low | No |
| % patients with protocol violations (PVs) | Dynamic | Yes | Medium | No |
| Compliance with diaries | Dynamic | Yes | High | Yes |
| Compliance with study drug | Dynamic | Yes | High | Yes |
| % evaluable patients by analysis population | Dynamic | Yes | Low | No |

Referring to FIG. 2, at act 210, one or more variables to be monitored during a clinical trial may be identified. For instance, in some embodiments, the candidate variables identified at act 205 (e.g., the illustrative candidate variables listed in Table 1) may be assessed, and one or more variables may be selected from the candidate variables based on one or more criteria. However, it should be appreciated that aspects of the present disclosure are not limited to selecting variables from candidate variables. In some embodiments, a variable may be derived from one or more candidate variables in a suitable manner.

In some embodiments, a candidate variable may be assessed to determine if the candidate variable is static (e.g., established before or at the beginning of a trial, and not changing significantly throughout the trial). Examples of static variables include, but are not limited to, site location, principal investigator (PI) demographics, PI specialty, etc. The inventors have recognized and appreciated that static variables may be more relevant to site selection at the outset of a trial, than to site monitoring during the trial.

In some embodiments, a candidate variable may be assessed to determine if the candidate variable is readily available for monitoring purposes. As an example, a data source (e.g., the illustrative clinical trial data source 105 shown in FIG. 1) may not provide sufficient information to allow tracking of a certain candidate variable. As another example, relevant information for a certain candidate variable may be scattered in various documents and/or datasets. It may not be practical or cost effective to collect and analyze the relevant information in near real time to track the candidate variable.

In some embodiments, candidate variables that are dynamic and readily available may be rated based on predictive power. For instance, in the example shown in Table 1, each candidate variable that is dynamic and readily available may be rated as having high, medium, or low predictive value for poor assay sensitivity.

In some embodiments, candidate variables with a high predictive value may be selected as variables to be monitored during a clinical trial. For instance, in the example shown in Table 1, three candidate variables are selected:

discordance between different measures of pain,
diary compliance, and
study drug administration compliance.

Referring to FIG. 2, at act 215, one of more of the variables identified at act 210 may be automatically validated. For instance, in some embodiments, data from one or more completed multicenter clinical trials (e.g., Phase 3 clinical trials) may be used to perform a retrospective analysis to evaluate whether a variable is predictive of poor assay sensitivity. Any suitable retrospective analysis technique may be used, such as regression analysis.

In some embodiments, data from multiple completed multicenter clinical trials on a same drug may be used to evaluate predictive value of a variable. As a non-limiting example, Table 2 below summarizes datasets from three multi-week randomized, double-blind, placebo-controlled trials of an analgesic drug dosed periodically (e.g., weekly, every 2 weeks, every 4 weeks, etc.). Two of the trials were conducted for a condition X, one of which was successful, while the other one failed. The third trial was a failed trial conducted for a condition Y, but the failure was borderline.

TABLE 2

Examples of datasets used to evaluate selected variables in retrospective analysis

| | Study A | Study B | Study C |
|---|---|---|---|
| Indication | Condition X | Condition Y | Condition X |
| Trial outcome | Successful | Failed (Borderline) | Failed |

In the example shown in Table 2, pain intensity (PI) scores were collected daily for 12 weeks using e-diaries in all three trials, which allows calculation of a change from baseline to endpoint in PI score. In one example, the baseline may represent Week 0 of the trial and the endpoint may represent Week 12 of the trial. In some embodiments, a PI score may be calculated by averaging PI scores for the last 7 days, 3 days, or any other number of days. In the two trials relating to condition X, the Western Ontario and McMaster University Osteoarthritis Index (WOMAC) questionnaire, which includes a subscale measuring pain on a 0-10 numerical rating scale (NRS), was also completed by subjects periodically (e.g., every week, every 2 weeks, every 4 weeks, etc).

In some embodiments, a variable to be monitored (e.g., as identified at act 210 of FIG. 2) may be operationalized for evaluation at different levels (e.g., subject, site, geographical region, etc.). For instance, the study drug administration adherence variable may be operationalized as "a proportion of subjects having missed at least one dose," "a proportion of missed doses across all subjects at a site," and/or "a proportion of missed doses across all subjects at all sites in a geographical region." As a non-limiting example, operational definitions of three variables (discordance between different measures of pain, diary compliance, and study drug administration compliance) at the subject level and at the site level are provided in Table 3 below.

TABLE 3

Examples of operational definitions of selected variables

| Selected Variable | Operational Definition (Measurements Made) | Comments |
|---|---|---|
| Subject-Level Quality Metrics | | |
| Subject missed doses | Number (%) of subjects having missed 0, 1, or 2 doses of investigational medicinal product (IMP) | For each subject N doses were expected (e.g., every 12/N weeks). All subjects had the first dose. |
| Subject non-compliance with e-diaries from baseline to desired endpoint (e.g., week 12) | Proportion of missed diary entries from baseline to desired endpoint | For example, if there were 2 entries per day for 13 weeks (1 baseline week + 12 weeks of treatment), resulting in 182 total entries, and a subject missed 10 entries, the proportion of missed entries would be 10/182. Note that this definition did not account for dropouts. |
| Subject non-compliance with e-diaries from baseline to desired endpoint (e.g., week 12) | Proportion of missed diary entries at baseline and desired endpoint | For example, if there were 2 entries per day for 2 weeks (Baseline and Week 12), resulting in 28 total entries, and a subject missed 10 entries, the proportion of missed entries would be 10/28. Note that this definition did not account for dropouts. |
| Discordance between measures of the same concept (e.g., PI NRS and WOMAC) | Baseline difference between scores expected to be similar (e.g., PI NRS score and WOMAC score) | Scores are normalized to the same scale. |
| Site-Level Quality Metrics | | |
| Site's proportion of missed doses | Proportion of missed doses at a site across subjects analyzed | For example, if a site only had one subject and that subject missed a dose, the proportion would be 1/N. If a site had three subjects and across the total number of 9 doses one was missed, the proportion would be ⅑N. |
| Site compliance with e-diaries | Proportion of missed diary entries from baseline to desired endpoint | Mean of subject-level values for this variable as stated above, across all subjects at a site. |
| Site compliance with e-diaries | Proportion of missed diary entries at baseline and desired endpoint | Mean of subject-level values for this variable as stated above, across all subjects at a site. |
| Subjects from high enrolling sites | Subjects from sites with ≥4 subjects | For each site, the number of subjects analyzed in this report was tallied. |

In some embodiments, the illustrative operational variables shown in Table 3 may be evaluated against the datasets from the three trials shown in Table 2. For instance, one or more statistics, such as mean, standard deviation (SD), median, and/or percentiles may be calculated. In some embodiments, a categorical variable may be evaluated, for example, by analyzing frequencies of certain subcategories.

In some embodiments, a regression analysis may be performed on change in PI score from baseline (e.g., Week 0) to endpoint (e.g., Week 12) assessing a treatment difference between placebo and active drug, controlling for baseline PI score, active treatment (active vs. placebo), baseline opioid use (use vs. non-use), baseline body weight (<85 kg vs.≥85 kg) (main model). One or more variables (e.g., the illustrative operational variables shown in Table 3) may be introduced as main effects and interaction terms (with active treatment vs. placebo) to determine whether the one or more variables are predictors. A coefficient of an interaction term (treatment×variable of interest) and corresponding p-value may be used as indicators of potential relevance of the variable to assay sensitivity.

In some embodiments, a p-value of 0.2 may be considered appropriate. It should be appreciated that aspects of the present disclosure are not limited to the use of a particular p-value, as other values may also be used (e.g., higher p values for less noisy data).

Overall, the above regression analysis showed that the following variables were associated with a decrease in assay sensitivity (P<0.2): (i) coming from a site that missed more doses; (ii) missing e-diary entries, especially at weeks 0 & 12; (iii) coming from a site with more missed e-diary entries, especially at weeks 0 & 12 (all p-values≤0.05); (iv) having discordant pain ratings between PI NRS and WOMAC Pain at baseline. Results of the regression analysis are shown in Table 4.

TABLE 4

Examples of P-values of interaction between variables and treatment effect (P-values < 0.2, indicating a treatment effect, shown in bold)

| Variables | Successful study relating to condition X | Failed (borderline) study relating to condition Y | Failed study relating to condition X |
|---|---|---|---|
| Subject missed doses | 0.722 | 0.6946 | 0.4776 |
| Site missed doses | 0.6508 | 0.1795 | 0.2887 |
| Subject e-diary non-compliance | 0.7476 | 0.5258 | 0.0675 |
| Subject e-diary non-compliance Weeks 0 and 12 | 0.5285 | 0.4627 | 0.0053 |
| Site e-diary non-compliance | 0.1663 | 0.1611 | 0.1357 |
| Site e-diary non-compliance Weeks 0 and 12 | 0.053 | 0.0461 | 0.0452 |

In sum, the regression analysis results confirmed that the three selected variables—e-diary compliance, study drug compliance, and discordance between pain scores—measured at a site level, predict which sites will fail to discriminate drug from placebo.

Figure 3A:
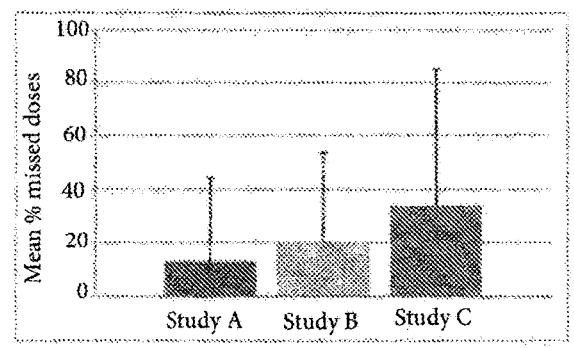
FIGS. 3A-3B show, respectively, mean percentage of missed doses and mean percentage of missed e-diary entries for the illustrative studies A-C summarized in Table 2, in accordance with some embodiments.
Figure 3B:
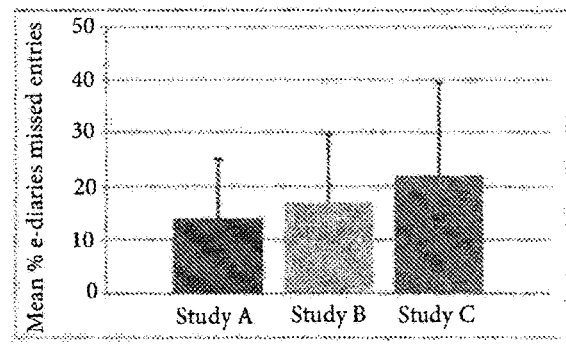

FIGS. 3A-3B show, respectively, mean percentage of missed doses (site level) and mean percentage of missed e-diary entries (site level) for the illustrative studies A-C summarized in Table 2, in accordance with some embodiments. As shown in FIGS. 3A-3B, the successful study (Study A) had the lowest number of missed doses at the site level (13% vs. 20% and 34%) and missed diary entries at the site level (16% vs. 18% and 29%), compared with the borderline and failed studies (Studies B and C, respectively).

It should be appreciated that the candidate variables and the selection process described above in connection with FIGS. 2, 3A-3B are provided solely for purposes of illustration. In various embodiments, one or more other variables may be proposed and/or selected in addition to, or instead of, the variables discussed herein. For instance, the selection and monitoring process is not limited to only candidate variables with high predictive values. In some embodiments, all or a subset of candidate variables with high predictive power may be selected and monitored first, followed by all or a subset of candidate variables with medium predictive power, and so on. Furthermore, different variables may be monitored in different studies, for example, depending on availability of relevant information, nature of study drug, etc.

The inventors have recognized and appreciated that statistical process control (SPC) techniques may be used to monitor one or more variables (e.g., one or more of the illustrative operational variables shown in Table 3) in near real time during a clinical trial. Traditionally, SPC techniques have been used to monitor and reduce variations in manufacturing processes (e.g., to reduce a rate of defective products from a production line). For instance, one or more measurable aspects of a manufacturing process may be monitored, and measurements collected over time may be analyzed using statistical techniques.

The inventors have recognized and appreciated that SPC techniques may be used to monitor performance of a subject, a trial site, a geographical region, and/or any other suitable constituent of a clinical trial, including the entire trial itself. For instance, a measurable aspect that is predictive of assay sensitivity (e.g., e-diary compliance, study drug compliance, discordance between pain scores, etc.) may be monitored, and measurements collected over time may be analyzed using statistical techniques to detect aberrant data patterns. An aberrant data pattern may be indicative of an issue to be corrected.

Figure 4:
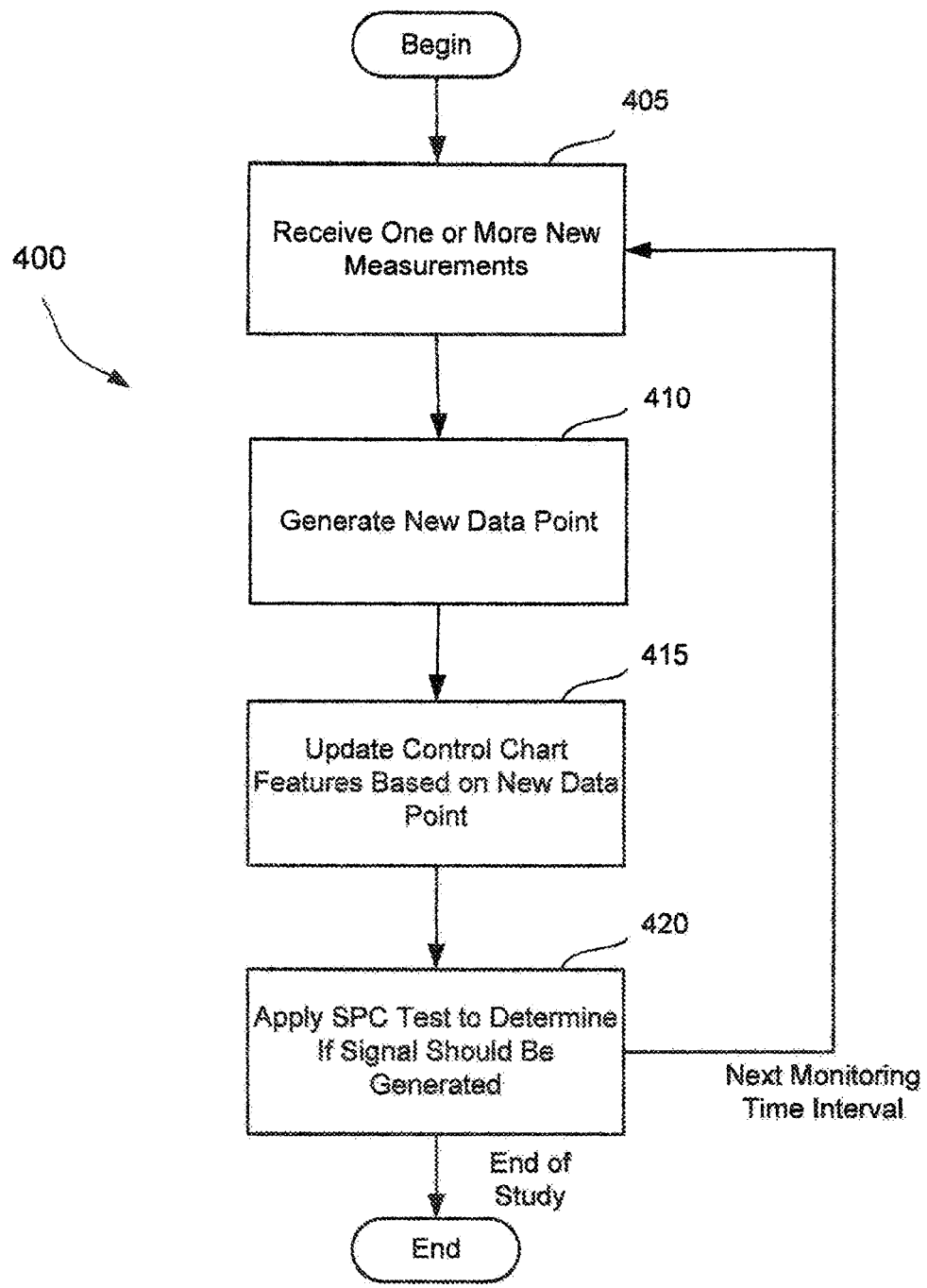
FIG. 4 shows an illustrative process 400 that may be performed to monitor and analyze a plurality of measurements collected over time, in accordance with some embodiments.

FIG. 4 shows an illustrative process 400 that may be performed to monitor and analyze a plurality of measurements collected over time, in accordance with some embodiments. For instance, the process 400 may be performed by the illustrative clinical trial data processing system 115 shown in FIG. 1 to process clinical trial data and generate one or more signals.

At act 405, one or more new measurements may be received from a clinical data store (e.g., the illustrative clinical data store 110 shown in FIG. 1). In some embodiments, clinical trial data may be collected periodically as indicated in a study protocol (e.g., daily, weekly, monthly, etc.) for multiple trial sites. For instance, the data may be collected by the illustrative clinical trial data source 105 shown in FIG. 1. Any suitable data may be collected, including, but not limited to, trial site operational/performance information (e.g., how long it takes for a site to respond to a query, turnover of workers, number of study protocol violations, etc.), subject reported information (e.g., diary entries, pain on a 0-11 scale), clinician reported information (e.g., whether subject's motor abilities improved), physical measurements (e.g., blood pressure), etc.

In some embodiments, trial site activity data and quality data may be collected at various time intervals. The trial site activity data may include data regarding a plurality of human subjects who were active at the trail site during each time interval. The trial site quality data may include data regarding a plurality of trial site quality metrics (e.g., the illustrative operational variables shown in Table 3). In some embodiments, the trial site quality data may indicate, for each time interval, a plurality of quality scores associated with the number of trial site quality metrics respectively. In some embodiments, subject status data may be collected at various time intervals. The subject status data may include data regarding respective statuses of a plurality of human subjects (e.g., a subject failed a screening test, had an adverse event, left the trial for another reason, is still active in the trial, etc.) at a plurality of trial sites participating in the clinical trial.

At act 410, one or more data points may be generated based on the one or more new measurements received at act 405. In some embodiments, a data point may be generated based on a measurement for a single variable. Alternatively, or additionally, a data point may be generated based on measurements corresponding respectively to multiple variables.

In some embodiments, a newly generated data point may be appended to a sequence of data points previously generated in a like manner based on prior measurements. Thus, as a clinical trial progresses, a timed sequence of data points may be generated, and variations may be detected and analyzed.

At act 415, one or more control chart features may be updated based on the timed sequence of data points updated at act 410. For instance, in some embodiments, a mean, a standard deviation, an upper control limit, and/or a lower control limit may be updated according to a suitable control chart definition. Non-limiting examples of control charts include individuals and moving range (ImR) or Shewhart charts, exponentially-weighted moving average (EWMA) charts, and p-charts. However, it should be appreciated that aspects of the present disclosure are not limited to the use of any particular control chart.

At act 420, an SPC test may be applied to distinguish non-random patterns from random patterns in the timed sequence of data points updated at act 410. In some instances, a non-random pattern may indicate an issue that should be corrected, whereas a random pattern may represent normal variations inherent in a clinical trial. When an SPC test is met, a signal may be generated and provided to a clinical trial analysis system (e.g., the illustrative clinical trial analysis system 120 shown in FIG. 1), which may process the signal and output one or more recommendations.

Non-limiting examples of SPC tests for generating signals are shown in Table 5 below. However, it should be appreciated that aspects of the present disclosure are not limited to the use of any particular test.

TABLE 5

Examples of SPC tests for signal generation

| # | Description of SPC test |
|---|---|
| 0a* | Point is below average line; all other SPC signals are ignored |
| 0b* | Point is above average line; all other SPC signals are ignored |
| 1 | Point is beyond control limit range or threshold |
| 2 | Two of previous three points are beyond ⅔ mark to control limit |
| 3 | Four or more points in a row are beyond ⅓ mark to control limit |
| 4 | Nine or more points in a row are on same side of average line |
| 5 | Four consecutive points going up, or four consecutive points going down |
| 6 | Four of previous five points going up, or four of previous five points down |
| 7 | Three points going in one direction, and then three points going in another direction (change of sign of slope) |

*Test 0a (or 0b) may be applied to certain variables for which performance below (or above) average line indicates better than average results, and therefore other SPC signals should be ignored.

In some embodiments, an SPC test may be used that references multiple timed sequences of data points. As an example, an SPC test may be met if: both a first condition is satisfied in a first timed sequence of data points, and a second condition is satisfied in a second timed sequence of data points. As another example, an SPC test may be met if: either a first condition is satisfied in a first timed sequence of data points, or a second condition is satisfied in a second timed sequence of data points.

Thus, in some embodiments, SPC tests may be used to generate signals based on: (i) particular event (e.g., occurrence of serious adverse event, protocol violation, etc.), (ii) particular variable reaching threshold (e.g., >5% wound infection rate, <80% e-diary compliance, etc.), and/or (iii) change in particular variable (e.g., change in distribution of values, detection of outliers to normally expected values, etc.). Such an SPC test may be defined to maintain a suitable balance between sensitivity (correctly identifying true positives) and specificity (correctly identifying true negatives).

FIGS. 5A-5B show illustrative control charts generated by applying SPC techniques to clinical trial data, in accordance with some embodiments. In this example, clinical trial data was analyzed in real-time to identify outliers and evaluate the clinical significance of those outliers.

FIGS. 5A-5B shows, respectively, an illustrative Shewhart chart 510 for subject diary non-compliance and an illustrative Shewhart chart 520 for discordance of different measures of pain, both generated for a same trial site. In the Shewhart charts 510 and 520, each dot may correspond to a respective time interval, For instance, each dot may correspond to a two-week interval or some other suitable time interval. Control limits, shown in FIGS. 5A-5B as gray bands, may be calculated from moving averages.

In the example of FIG. 5A, the illustrative Shewhart chart 510 depicts a sequence of data points to which one or more SPC tests from the illustrative SPC tests in Table 5 are applied. When all SPC tests are not met for a data point, that data point may be colored green (e.g., data points 512). For instance, data points within a particular control limit range (e.g., between 0-1.5) are shown colored green. When any SPC test is met for a data point, that data point may be colored red (e.g., data points 514). For instance, data points outside the control limit range are shown colored red. One or both of the SPC tests #1 and #5 may be met for these data points.

In the example of FIG. 5B, the illustrative Shewhart chart 520 depicts a sequence of data points to which one or more SPC tests from the illustrative SPC tests in Table 5 are applied. In this example, although all the data points are within a particular control limit range, the SPC test #4 may be met because nine or more points in a row are on the same side of the average line. Therefore, all the data points 522 before the ninth data point on the same side of the average line (for which all SPC tests are not met) may be colored green or yellow, and the ninth and successive data points 524 (for which the SPC test #4 is met) may be colored red, until a data point for which the SPC test #4 is not met is encountered.

In some embodiments, signals may be generated by a clinical trial data processing system (e.g., the illustrative clinical trial data processing system 115 in the example of FIG. 1) for the red colored data points shown in the Shewhart charts 5A and 5B.

It should be appreciated that the present disclosure is not limited to the use of a particular type of SPC test or a particular type of control chart, as other SPC tests and control charts may be used additionally or alternatively.

Thus, the inventors have recognized and appreciated that SPC techniques may be used retrospectively to categorize variables (e.g., by identifying correlation between variables). Additionally, or alternatively, SPC techniques may be used to monitor certain variables while a clinical trial is on-going, to identify trends and/or abnormalities. This may allow early detection of site performance issues, so that appropriate corrective actions may be implemented.

Although examples of control charts are shown in FIGS. 5A-5B, it should be appreciated that aspects of the present disclosure are not limited to rendering a control chart visually. Various control chart features (e.g., mean, standard deviation, upper control limit, lower control limit, etc.) may be calculated and used to generate signals, without being visually rendered.

In some embodiments, control chart features and/or results of SPC tests may be used to generate quality scores associated with trial site quality metrics (e.g., subject-level, site-level, and/or multi-site quality metrics). For instance, a quality score may be generated that ranges between 0-5, where 0 may be indicative of lowest quality and 5 may be indicative of highest quality. For example, various control chart features and/or results of SPC tests may indicate that a trial site is experiencing low diary compliance average relative to other trial sites, and a quality score of "1" for that trial site may be generated, indicative of low quality. On the other hand, a very high diary compliance average at a certain trial site relative to other trial sites may result in a quality score of "5" for the trial site, indicative of high quality. Any suitable scoring mechanism may be used, as aspects of the present disclosure are not so limited. In some embodiments, a quality score associated with a composite quality metric may include a weighted sum of two or more quality scores associated respectively with two or more constituent quality metrics.

In some embodiments, quality scores associated with trial site quality metrics may be generated by a clinical trial analysis system. With reference to the example shown in FIG. 1, the illustrative clinical trial analysis system 120 may receive signals from the illustrative clinical trial data processing system 115, and may generate quality scores based on the received signals. For instance, an SPC test performed by the clinical trial data processing system 115 may generate a signal based on diary compliance of a trial site reaching a particular threshold (e.g., <80% e-diary compliance). This signal may be communicated to the clinical trial analysis system 120, which may generate a quality score by applying appropriate rules (e.g., diary compliance rules) to the signal. Additionally, or alternatively, the clinical trial analysis system 120 may generate recommendations regarding a trial site (e.g., an intervention to address a quality issue at the trial site, removal of the trial site from an on-going clinical trial or future clinical trials due to the quality issue, etc.).

In some embodiments, while the clinical trial analysis system 120 may generate quality scores for a large number of quality metrics, the clinical trial analysis system 120 may generate a recommendation only if a quality score falls below a threshold for a quality metric from a selected subset of quality metrics. Such a quality metric may be referred to herein as a "triggering" quality metric. For instance, a triggering quality metric may be selected that is highly predictive of assay sensitivity. Examples of triggering quality metrics include, but are not limited to, daily pain score variability, discordance between different measures of pain, inversions of worst pain scores and average pain scores (where the worst pain is lower than average pain), e-diary noncompliance, and study drug administration noncompliance In some embodiments, a recommendation may be informed by a quality score of a non-triggering quality metric (also referred to herein as a "supporting" quality metric). Examples of support quality metrics include, but are not limited to, number of protocol deviations, time to query response, time to query resolution, number of queries, and data entry time.

Figure 6:
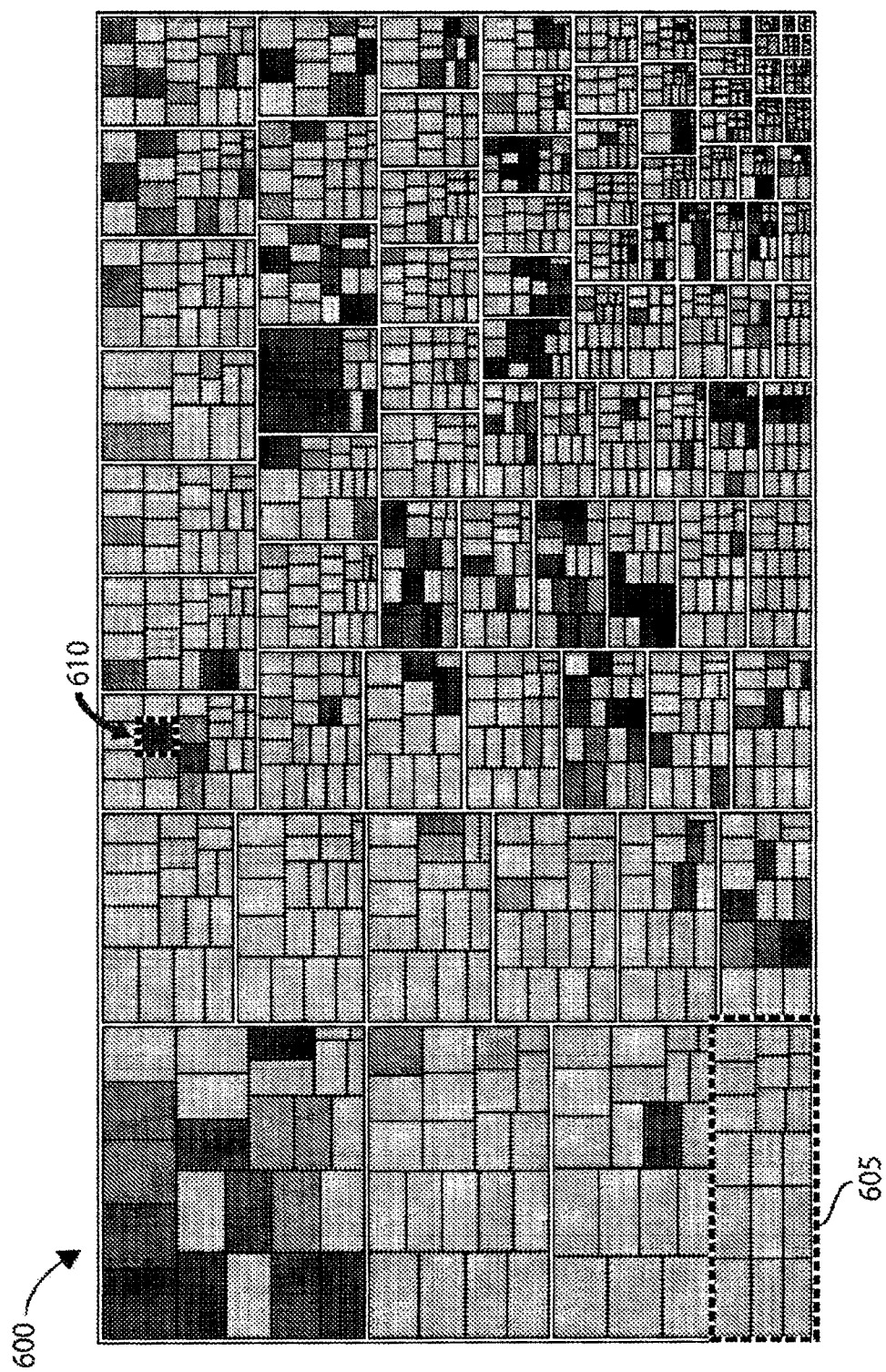
FIG. 6 shows an illustrative visual representation 600 of clinical trial data, in accordance with some embodiments.

FIG. 6 shows an illustrative visual representation 600, in accordance with some embodiments. For instance, the visual representation 600 may represent results produced by the illustrative clinical trial analysis system 120 shown in FIG. 1.

The inventors have recognized and appreciated that performance of trial sites throughout a clinical trial may be visualized as shown in FIG. 6 to identify sites with potential operational and/or other problems affecting assay sensitivity or specificity (e.g., the clinical trial's ability to distinguish active drug from placebo). In this example, the visual representation 600 includes a plurality of regions, such as region 605. Each region may correspond to a respective trial site.

In some embodiments, a region may include a plurality of sub-regions, such as sub-region 610. Each sub-region may correspond to a respective time interval. For instance, each sub-region may correspond to a two-week interval, so that a region corresponding to a trial site that has participated in a trial for 26 weeks may have 13 sub-regions. In some instances, there may be fewer than 13 sub-regions, as there may be one or more two-week intervals during which there was no active subject at that trial site.

In the example shown in FIG. 6, regions and sub-regions are drawn as rectangular boxes. However, it should be appreciated that aspects of the present disclosure are not limited to the use of any particular shape, as one or more other shapes (e.g., triangles, circles, hexagons, etc.) may be used in addition to, or instead of, rectangles.

In some embodiments, a size of a sub-region may be determined based on a number of active subjects at the corresponding trial site during the corresponding time interval (e.g., subjects who visited or otherwise interacted with the trial site during the time interval), and/or some other metric indicating an amount of data available for analysis (e.g., another quantifiable parameter). In this manner, a region corresponding to a trial site enrolling more patients may be larger in size than a region corresponding to a trial site enrolling fewer patients. This may help a user appreciate an extent of a detected quality issue when viewing the visual representation 600. For instance, in some embodiments, an indication of a quality issue may be provided by showing a sub-region in a certain fill pattern or color (e.g., red for a low quality score such as 0, green for a high quality score such as 5, etc.). Thus, a larger sub-region showing a fill pattern or color associated with a quality issue may indicate more subjects and/or more data being affected by the quality issue. Examples of fill patterns include, but are not limited to, hatching, cross hatching, stippling, etc.

In the example shown in FIG. 6, regions corresponding to different trial sites are arranged spatially according to size (e.g., sum of all sub-regions with each region). For instance, the top left region may correspond to the largest trial site in terms of number of patients enrolled (and/or some other metric indicative of an amount of available data), and the bottom right region may correspond to the smallest trial site. However, that is not required, as in some embodiments, regions may be arranged according to trial site location, which may facilitate identification of geographical trends. Additionally, or alternatively, regions may be arranged according to treatment group, vendor group, etc., to provide additional details on how such groups performed throughout a trial.

In some embodiments, a fill pattern density or color intensity may be varied according to severity of a detected quality issue. As a non-limiting example, a more dense fill pattern of a first kind (or a more intense red color) in certain sub-regions may indicate a severe quality issue (e.g., very low diary compliance average at a certain trial site relative to other trial sites), and a more dense fill pattern of a second kind (or an intense green color) in certain sub-regions may indicate high quality (e.g., very high diary compliance average at a certain trial site relative to other trial sites).

It should be appreciated that aspects of the present disclosure are not limited to the use of any particular quality metric. For instance, in some embodiments, multiple visual representations may be rendered to a user, each using a different quality metric of interest. Furthermore, a quality metric may be based on a single variable or multiple variables. Examples of variables include, but are not limited to, a number of active subjects, a number of events of a certain type, a difference between measurements of a same type but taken at different time points, a difference between measurements of different types taken at a same time point, etc.

It should also be appreciated that aspects of the present disclosure are not limited to the use of sub-regions corresponding to time intervals, or to the use of any sub-region at all. In some embodiments, a sub-region or other indicium (e.g., dot, pin, flag, etc.) may be provided for each individual subject, and a visual indication (e.g., fill pattern or color) may be provided to indicate the subject's status in a clinical trial (e.g., the subject failed a screening test, had an adverse event, left the trial for another reason, is still active in the trial, etc.). In some embodiments, an intervention may be recommended based on the status of the subject. In one example, an intervention may include re-training the subject to comply with study protocol. In another example, an intervention may include excluding the subject from the clinical trial.

The inventors have recognized and appreciated that visual representations such as the illustrative visual representation 600 shown in FIG. 6 may help a user quickly distinguish trial sites that performed normally throughout a clinical trial from those that were consistently abnormal. This may not only save the user time, but also reduce usage of resources, such as computing resources associated with generating, displaying, and/or printing lengthy reports regarding performance of various trial sites.

Additionally, visual representations such as the illustrative visual representation 600 may help a user identify a percentage of time that any trial site showed abnormal behavior, and/or if that abnormal behavior was grouped in time or distributed throughout a duration of a clinical trial. For example, if a trial site is mostly green, but has some strong red sub-regions that are clustered together, a user may infer that there was an issue at that trial site during a few consecutive weeks, but the trial site behaved normally throughout most of the trial. In contrast, a trial site where most sub-regions are red may indicate that the trial site had consistent quality issues throughout the trial.

It should be appreciated that aspects of the present disclosure are not limited to the details shown in FIG. 6 and discussed above. For instance, in some embodiments, fill patterns may be used to convey information regarding sub-regions, in addition to, or instead of, colors. For example, different fill patterns may be used to indicate different types of quality issues, and/or different density of a fill pattern may be used to indicate different levels of severity of a quality issue.

As discussed above in connection with FIG. 1, a subject-level signal may be generated based on a percentage of diary entries that are actually filled, out of all diary entries that a subject is expected to fill, to track one or more endpoints of interest (e.g., a certain type of pain), and a site-level signal may be generated by averaging subject-level diary compliance signals over all subjects active in a certain period of time (e.g., one week, two weeks, three weeks, one month, etc.). In this manner, a low site-level signal may indicate that, on average, active subjects at a trial site did not fill their diaries as required by a study protocol.

As an example, a diary compliance signal may be calculated on a bi-weekly basis for each subject, so that a subject-level percentage may indicate for how many days out of the 14 days there was an entry in the subject's diary. The entry may record any one or more endpoints of interest, such as average pain level (e.g., on a scale of 0-10) that the subject felt. A site-level average signal may then be generated and used to determine a fill pattern and/or density, or a color and/or intensity, for each sub-region corresponding to a 14-day period. For instance, low diary compliance (e.g., below a selected threshold) may be show in red, and high diary compliance (e.g., above a selected threshold) may be show in green. A size of a sub-region may be determined based on a number of active subjects at the relevant site during the relevant 14-day period.

Figure 7:
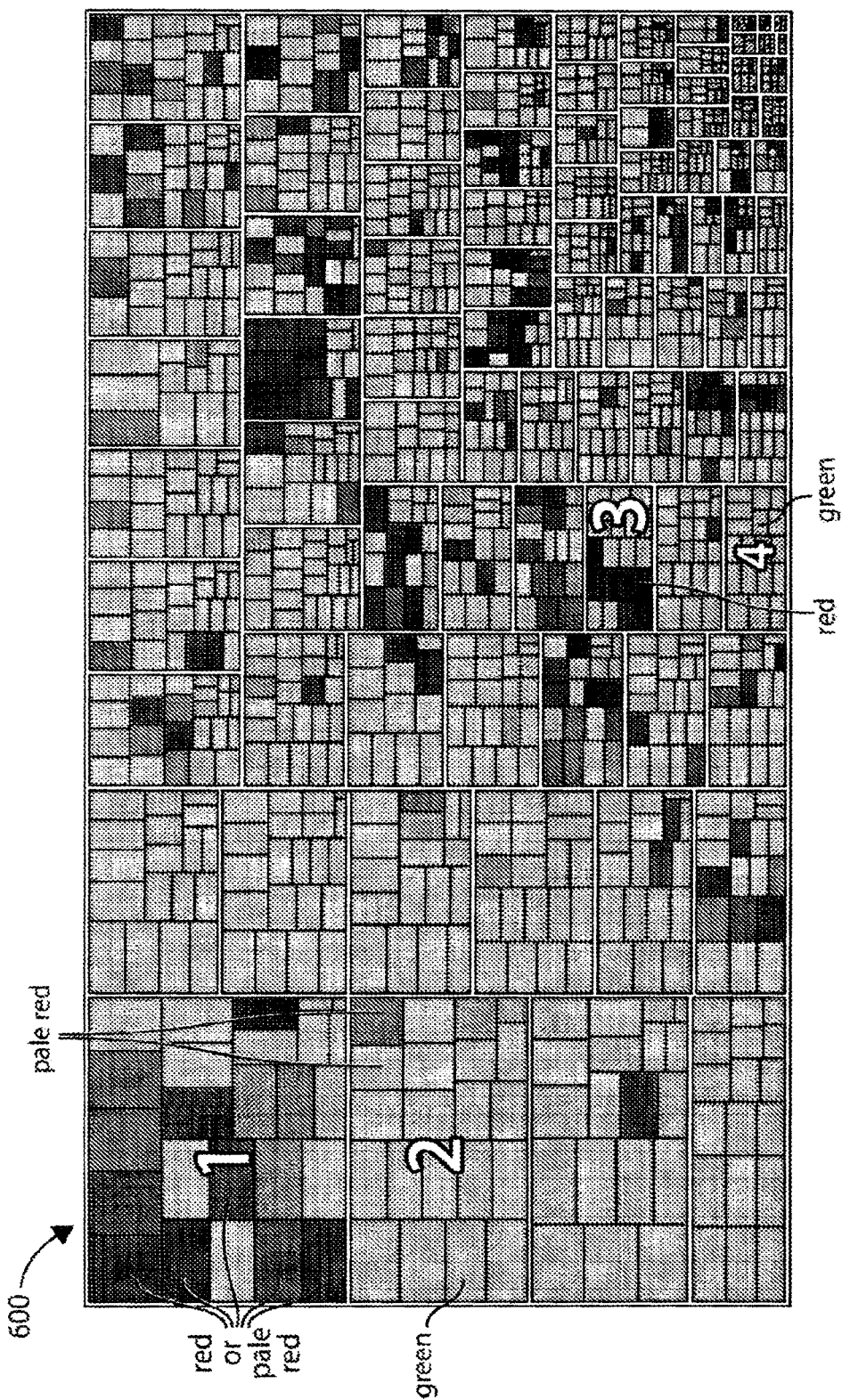
FIG. 7 shows the illustrative visual representation 600 with illustrative regions 1-4, corresponding respectively to four different trial sites, in accordance with some embodiments.

FIG. 7 shows the illustrative visual representation 600 with illustrative regions 1-4, corresponding respectively to four different trial sites, in accordance with some embodiments. In this example, site 1 is a large site (e.g., with many active subjects throughout a trial), and may have had subject diary compliance issues during many bi-weekly periods (e.g., sub-regions colored red or pale red). Site 2 may be another large site, but may only have had a few bi-weekly periods with subject diary compliance issues, and those issues may appear to have been minor (e.g., sub-regions colored pale red). Site 3 may be a small site that went through a period of significant diary compliance issues (e.g., sub-regions colored deep red), but it may appear that those issues were limited to only parts of a study timeline. Site 4 may be another small site, and may have had no subject diary compliance issue at all (e.g., sub-regions colored green).

The inventors have recognized and appreciated that, when evaluating site performance, sites such as sites 2 and 4 may be more desirable than the others, because of consistent high performance. Site 3 may still be a suitable candidate for other clinical trials, depending on a careful analysis of what led to the issues observed there. Site 1 may be a large site that had consistent issues, and more careful monitoring may be recommended to determine if site 1 is suitable for upcoming trials. Accordingly, the representation may be used to identify sites to be removed from this or a future trial, or that are in need of corrective action in the present trial or a future trial, such as but not limited to staff/personnel training. In some embodiments, quality scores may also be used to weigh data contributed by a suspect site (e.g., one which demonstrates suboptimal and potentially non-random performance) in an existing or a future trial.

FIGS. 8A-8D show illustrative visual representations 800A-800D, in accordance with some embodiments. For instance, the visual representations 800A-800D may be generated by the illustrative clinical trial analysis system 120, and may be displayed to a user via the illustrative clinical trial monitoring user interface 125, as shown in FIG. 1.

The inventors have recognized and appreciated that performance of a trial site throughout a clinical trial may be visualized as shown in FIGS. 8A-8D to determine whether the site has potential problems affecting assay sensitivity or specificity. In this example, each of the FIGS. 8A-8D shows performance of a different trial site. For instance, visual representation 800A may represent the performance of trial site A, visual representation 800B may represent the performance of trial site B, visual representation 800C may represent the performance of trial site C, and visual representation 800D may represent the performance of trial site D.

In the example of FIGS. 8A-8D, each of the visual representations 800A-800D includes a plurality of regions, such as regions 805, 810, and 815. Each region may correspond to a respective quality metric. As a non-limiting example, a quality metric (e.g., shown as Metric 1) may be a subject-level or site-level quality metric associated with one or more of the illustrative operational variables shown in Table 3. As another example, a quality metric (e.g., shown as Metric 2) may be a site performance metric, such as median time to query response, recruitment rate, etc. As another example, a quality metric (e.g., shown as Metric 3) may be a supporting metric.

In some embodiments, a quality metric may be based on measurements associated with a single variable. Such a metric may be referred to herein as a "univariate" metric. Additionally, or alternatively, a quality metric may be used that is based on measurements associated, respectively, with multiple variables. Such a metric may be referred to herein as a "multivariate" metric.

In some embodiments, a region may include a plurality of sub-regions, such as sub-region 830. Each sub-region may correspond to a respective time interval. For instance, each sub-region may correspond to a two-week interval, so that a region corresponding to a trial site that has participated in a trial for 26 weeks may have 13 sub-regions. In some instances, there may be fewer than 13 sub-regions, as there may be one or more two-week intervals during which there was no active subject at that trial site.

In the example shown in FIGS. 8A-8D, regions and sub-regions are drawn as rectangular boxes. However, it should be appreciated that aspects of the present disclosure are not limited to the use of any particular shape, as one or more other shapes (e.g., triangles, circles, hexagons, etc.) may be used in addition to, or instead of, rectangles.

In some embodiments, a size of a sub-region may be determined based on a number of active subjects at the corresponding trial site during the corresponding time interval (e.g., subjects who visited or otherwise interacted with the trial site during the time interval), and/or some other value indicating an amount of data available for analysis.

In some embodiments, an indication of a quality issue may be provided by showing a sub-region with a certain fill pattern or color (e.g., red for a low quality score such as 0, yellow for a medium quality score such as 3, and green for a high quality score such as 5, etc.). In some embodiments, a fill pattern density, or a color intensity, may be varied according to severity of a detected quality issue. As a non-limiting example, a more dense fill pattern of a first kind, or a more intense red color, may indicate a severe quality issue (e.g., very low diary compliance average, or high screen failure and/or withdrawal rates), and a more dense fill pattern of a second kind, or an intense green color, may indicate high quality (e.g., very high diary compliance average, or very low screen failure and/or withdrawal rates).

In some embodiments, the sub-regions associated with each region may be ordered chronologically. For instance, time may run from left to right, and then from top to bottom, so that the upper left-most sub-region may correspond to the earliest time interval and the bottom right-most sub-region may correspond to the latest time interval.

In some embodiments, the sub-regions associated with each region may be organized based on quality scores. As one example, all sub-regions colored red may be grouped together, and all sub-regions colored green may be grouped together. Within each group, the sub-regions may be arranged with increasing or decreasing intensity. As another example, sub-regions may be grouped together based on fill pattern. Within each group, the sub-regions may be arranged with increasing or decreasing density. Organization of sub-regions in this manner may facilitate quick identification of quality issues associated subject-level, site-level, and/or other quality metrics.

The inventors have recognized and appreciated that visual representations such as the illustrative visual representations 800A-800D may help a user quickly determine how a particular site is performing across multiple quality metrics during a clinical trial. This may in turn facilitate distinguishing trial sites that are performing well from those that are not. As one example, the visual representation 800A of FIG. 8A may indicate that trial site A behaved normally and had almost no quality issues across the different quality metrics (Metric 1, Metric 2, and Metric 3) throughout the study timeline. Based on the visual representation 800A, a user may infer that trial site A had good performance (e.g., sub-regions colored primarily green or yellow) across the different quality metrics, and that no intervention may be needed.

Figure 8B:
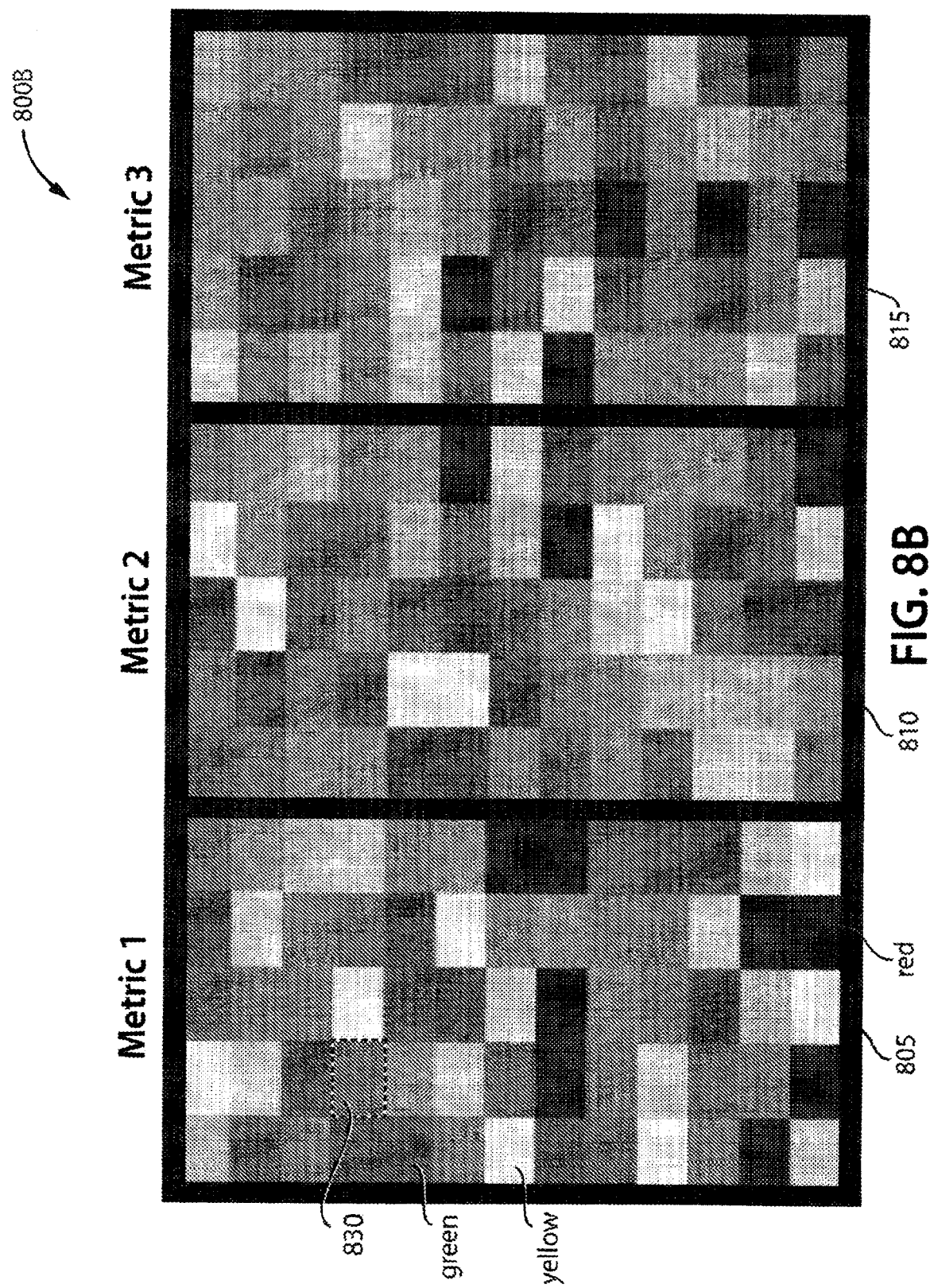

As another example, the visual representation 800B of FIG. 8B may indicate that trial site B had a few bi-weekly periods (e.g., sub-regions colored red) with quality issues for each metric. Based on the visual representation 800B, a user may infer that, while trial site B had some quality issues, overall trial site B still performed well, and that no intervention may be needed.

Figure 8C:
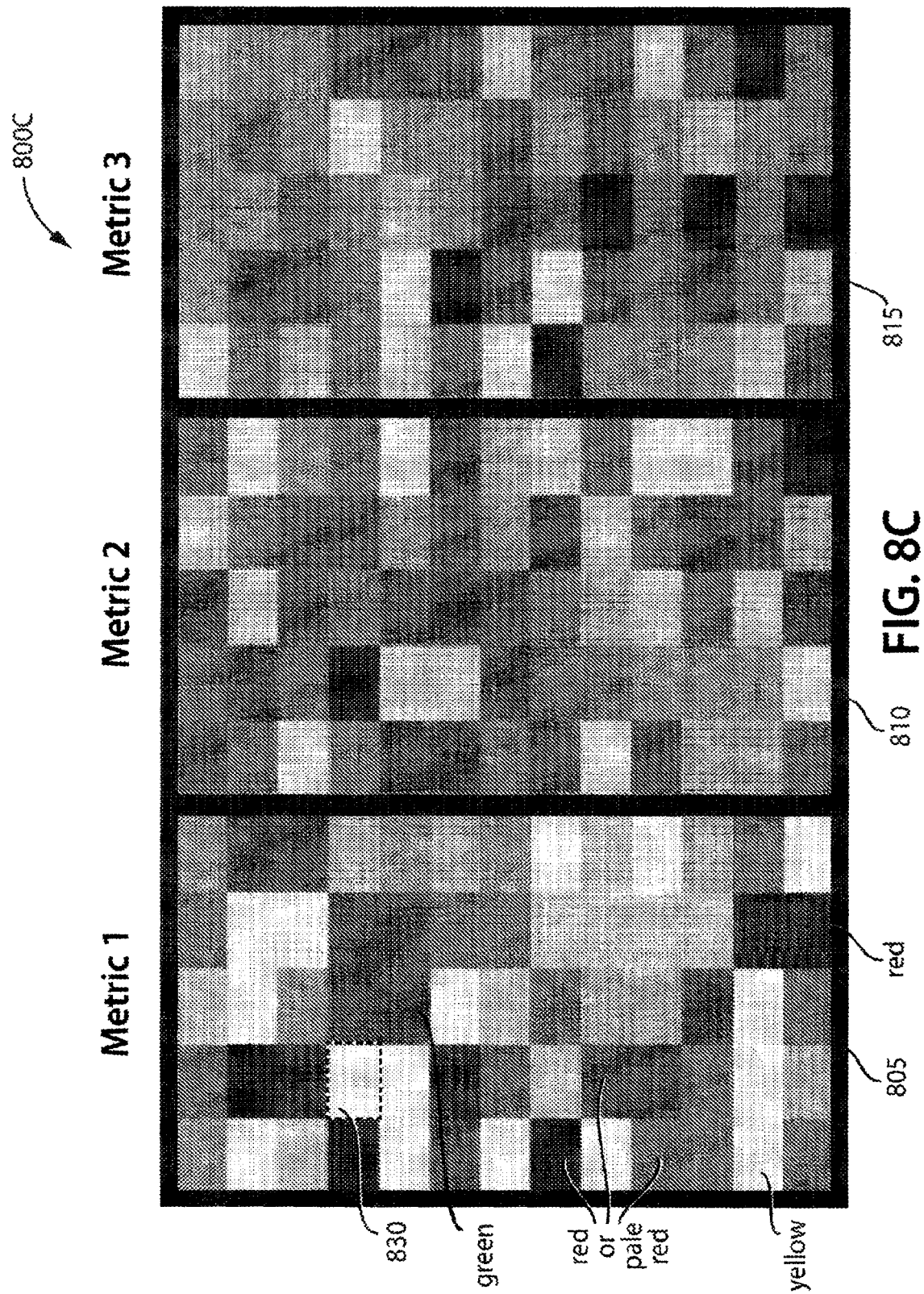

As another example, the visual representation 800C of FIG. 8C may indicate that, while trial site C had few bi-weekly periods (e.g., sub-regions colored red) with quality issues for Metrics 2 and 3, trial site C had many bi-weekly periods with quality issues for Metric 1. Based on the visual representation 800C, a user may infer that trial site C had significant quality issues for Metric 1, and that further evaluation may be needed to determine whether intervention may be appropriate.

Figure 8D:
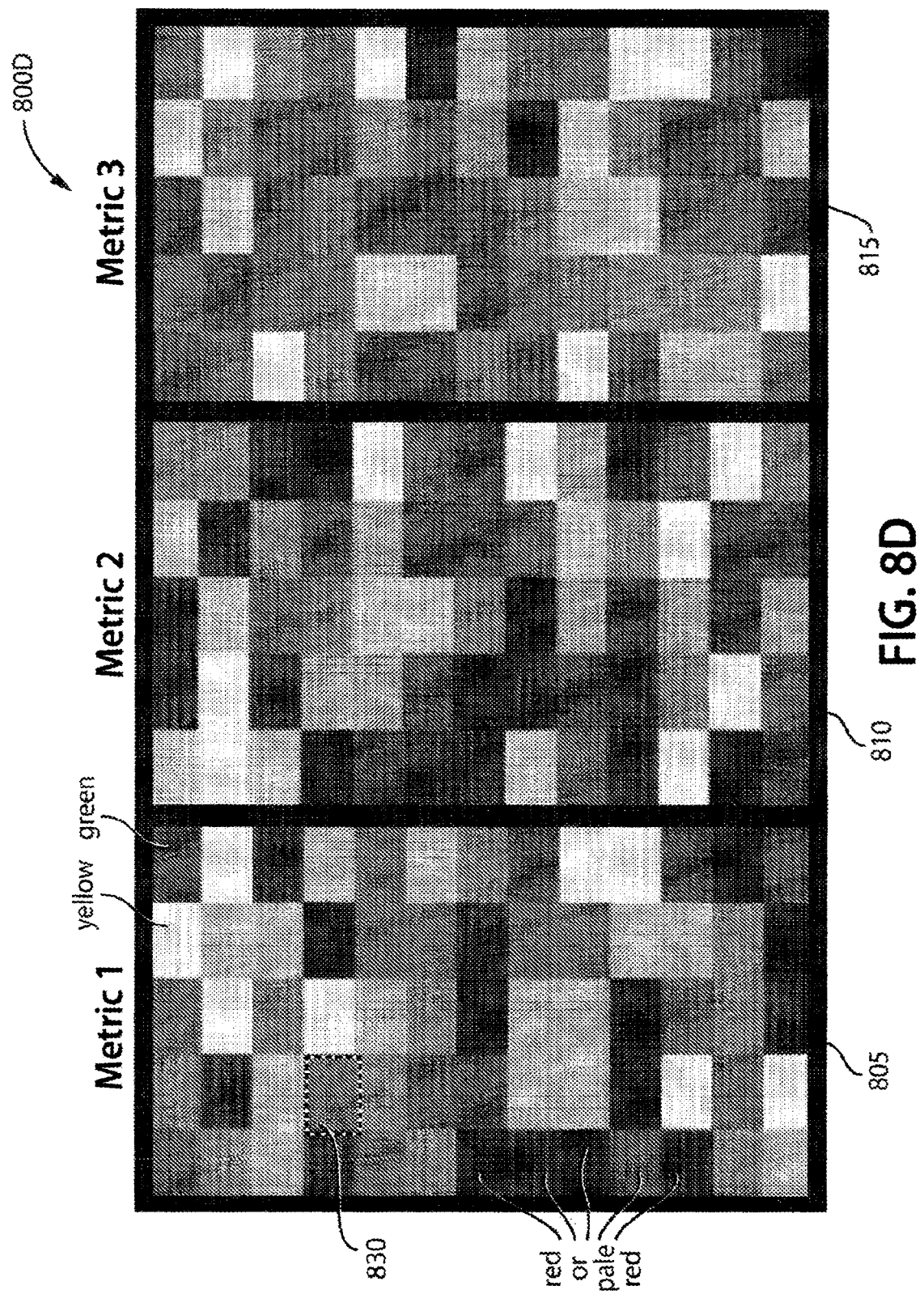

As another example, the visual representation 800D of FIG. 8D may indicate that trial site D had many bi-weekly periods (e.g., sub-regions colored red or pale red) with quality issues for Metrics 1 and 2. Based on the visual representation 800D, a user may infer that trial site D had significant quality issues for Metrics 1 and 2, and that intervention may most likely be appropriate.

In some embodiments, trial sites may be ranked based on their performance. A ranking may be generated based on, for example, a percentage of red colored sub-regions in each region corresponding to a quality metric. A trial site (e.g., trial site D) may be ranked lowest due to the highest percentage of red colored sub-regions across all metrics. Similarly, a trial site (e.g., trial site A) may be ranked highest due to the lowest percentage of red colored sub-regions across all metrics. In this manner, quality rankings may be determined by performing image analysis on visual representations such as the illustrative visual representations 800A-800D of FIGS. 8A-8D, in addition to, or instead of, analyzing the underlying data (e.g., quality scores) used to generate the visual representations 800A-800D. In some embodiments, the underlying data may be used to determine the quality rankings even when visual representations are not generated.

In some embodiments, because the boundaries of regions 805, 810, and 815 remain the same across the visual representations 800A-800D, image analysis techniques may be used to compare the visual representations 800A-800D. In some embodiments, additional information may be conveyed via a visual representation, such as additional dimensions for multivariate metrics, information regarding human subjects who were active at a trial site and/or during a time interval, etc. In some embodiments, such information may be encoded as pixels at selected locations in each sub-region.

Figure 9A:
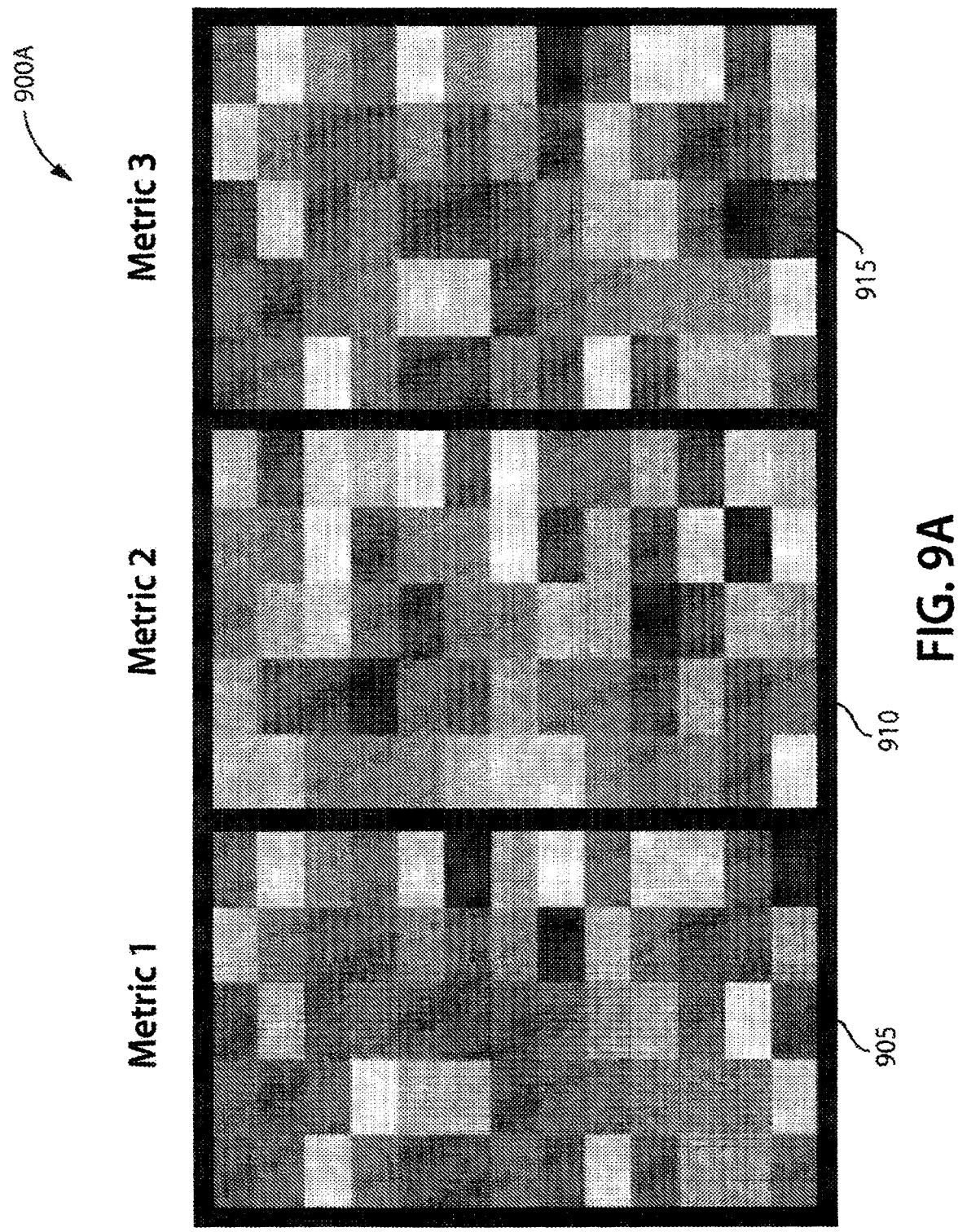
FIGS. 9A-9B show illustrative visual representations 900A-900B to facilitate comparison between trial sites having different characteristics, in accordance with some embodiments.
Figure 9B:
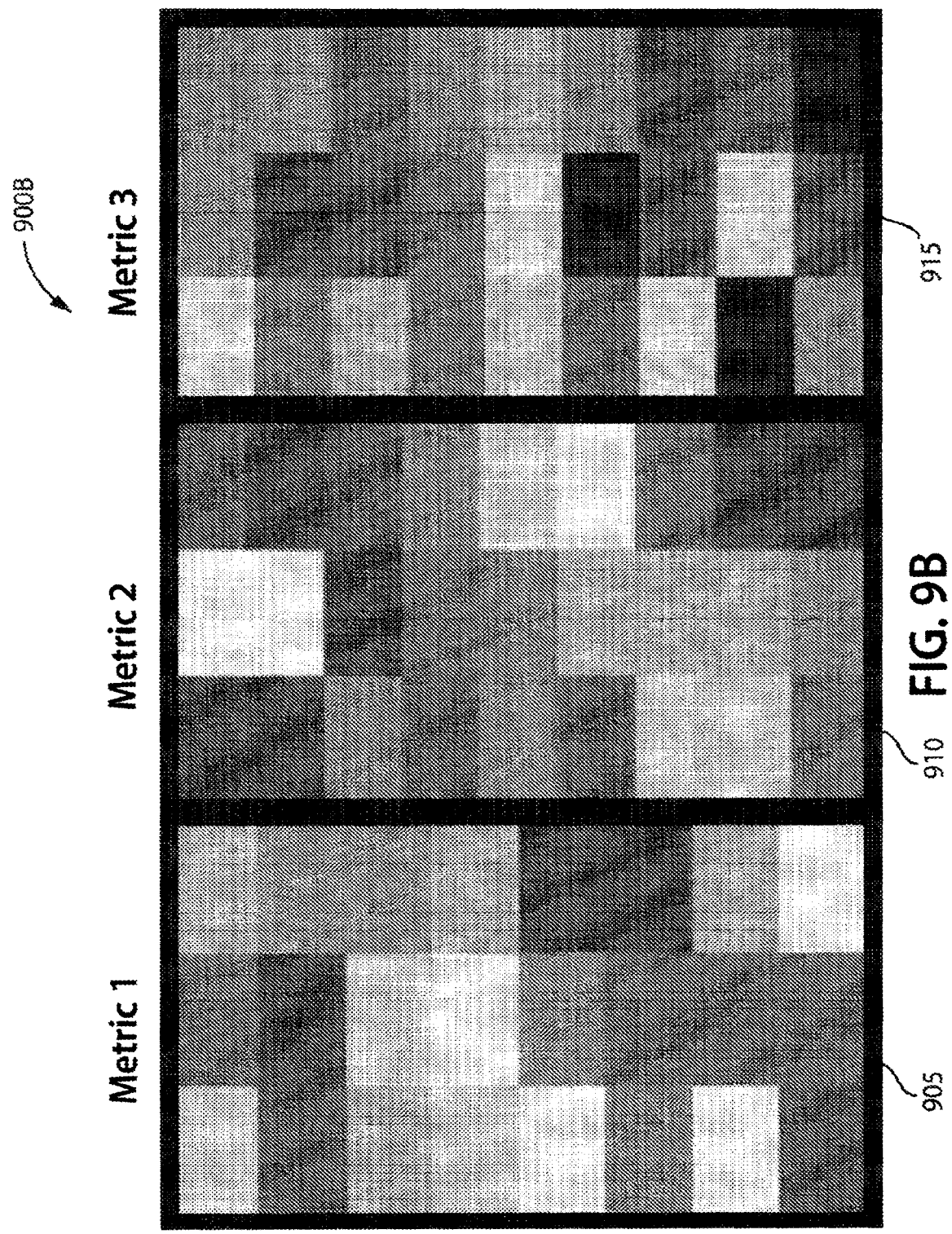

FIGS. 9A-9B show illustrative visual representations 900A-900B, in accordance with some embodiments. For instance, the visual representations 900A-900B may be generated by the illustrative clinical trial analysis system 120, and may be displayed to a user via the illustrative clinical trial monitoring user interface 125, as shown in FIG. 1. In some embodiments, the visual representation 900A may be generated based on performance of trial site A, whereas the visual representation 900B may be generated based on performance of a different trial site, trial site B.

In the example of FIGS. 9A-9B, each visual representation 900A-900B includes a plurality of regions, such as regions 905, 910, and 915. Each region may correspond to a respective quality metric, and may include a plurality of sub-regions. Unlike the example of FIGS. 8A-8D, the regions 905, 910, and 915 in FIGS. 9A-9B have sub-regions of different sizes. For instance, sub-regions of the region 905 in FIG. 9A may be smaller than sub-regions of the region 905 in FIG. 9B. Since the region 905 has the same size in both visual representations, the region 905 has more sub-regions in FIG. 9A than in FIG. 9B.

The inventors have recognized and appreciated that visual representations such as the illustrative visual representations 900A-900B may help a user quickly compare different trial sites having different characteristics such as duration of participation in a clinical trial, number of active subjects, etc. For instance, each sub-region in the region 905 may represent a bi-weekly period, and trial site A may have participated for a longer period of time than trial site B. Thus, the region 905 may have more sub-regions in FIG. 9A than in FIG. 9B. By keeping the overall area of the region 905 the same between FIG. 9A and FIG. 9B, data from the two sites may be normalized to the same scale. This may facilitate a visual comparison (or a comparison based on image analysis) between trial site A and trial site B, even though the data from the two sites may not be directly comparable due to the different durations of participation.

In some embodiments, one or more of the comparison techniques described above in connection with FIGS. 9A-9B may be used to compare visual representations corresponding to different trials having differing lengths at a same trial site or different trial sites. In some embodiments, a comparison of two trial sites may be possible even if visual representations for the trial sites are generated based on different quality metrics. For instance, two different trial sites may have been used, respectively, to conduct trials on drugs for treating different conditions. Quality metrics monitored at these trials may be different, and therefore quality scores for the two sites may not be directly comparable. As one example, Metric 1 in FIG. 9A may be a NRS pain score, whereas Metric 1 in FIG. 9B may be a WOMAC pain score. As another example, Metrics 1 and 2 may correspond respectively to scores from two different instruments designed to measure a similar symptom (e.g., sleep disruption). Nevertheless, a visual comparison between the visual representations 900A-900B may be possible.

It should be appreciated that aspects of the present disclosure are not limited to the use of colors, color intensities, fill patterns, or fill pattern densities to convey information. In some embodiments, one or more other visual indications such as border style may be used. As an example, a particular color applied to a sub-region may depict a first quality metric (e.g., with color intensity indicating whether a quality score for that metric is high or low), a particular fill pattern applied to the sub-region may depict a second quality metric (e.g., with fill pattern density indicating whether a quality score for that metric is high or low), a particular border pattern applied to the sub-region may depict a third quality metric. In another example, a first color applied to a first portion of a sub-region may depict a first quality metric, and a second color applied to a second portion of the sub-region may depict a second quality metric.

It also should be appreciated that aspects of the present disclosure are not limited to the use of two-dimensional visual representations. In some embodiments, visual representations of higher dimensions may be used, for example, to display multivariate metrics. Additionally, or alternatively, visual representations of higher dimensions may be used to provide additional information, such as information regarding human subjects who were active at a trial site.

Figure 10:
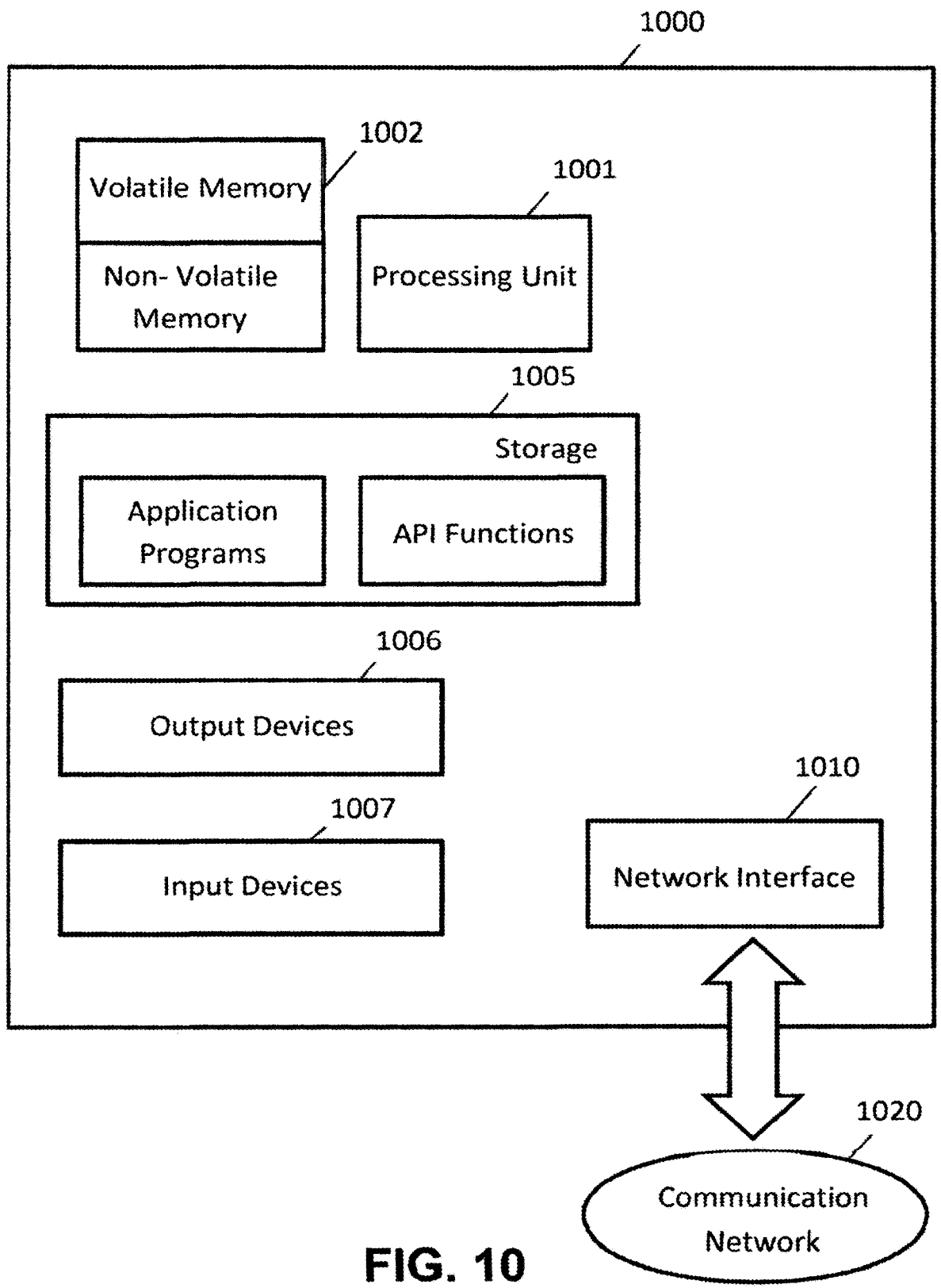
FIG. 10 shows, schematically, an illustrative computer 1000 on which any aspect of the present disclosure may be implemented.

FIG. 10 shows, schematically, an illustrative computer 1000 on which any aspect of the present disclosure may be implemented. In the embodiment shown in FIG. 10, the computer 1000 includes a processing unit 1001 having one or more processors and a non-transitory computer-readable storage medium 1002 that may include, for example, volatile and/or non-volatile memory. The memory 1002 may store one or more instructions to program the processing unit 1001 to perform any of the functions described herein. The computer 1000 may also include other types of non-transitory computer-readable medium, such as storage 1005 (e.g., one or more disk drives) in addition to the system memory 1002. The storage 1005 may also store one or more application programs and/or external components used by application programs (e.g., software libraries), which may be loaded into the memory 1002.

The computer 1000 may have one or more input devices and/or output devices, such as devices 1006 and 1007 illustrated in FIG. 10. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards and pointing devices, such as mice, touch pads, and digitizing tablets. As another example, the input devices 1007 may include a microphone for capturing audio signals, and the output devices 1006 may include a display screen for visually rendering, and/or a speaker for audibly rendering, recognized text.

As shown in FIG. 10, the computer 1000 may also comprise one or more network interfaces (e.g., the network interface 1010) to enable communication via various networks (e.g., the network 1020). Examples of networks include a local area network or a wide area network, such as an enterprise network or the Internet. Such networks may be based on any suitable technology and may operate according to any suitable protocol and may include wireless networks, wired networks or fiber optic networks.

Having thus described several aspects of at least one embodiment, it is to be appreciated that various alterations, modifications, and improvements will readily occur to those skilled in the art. Such alterations, modifications, and improvements are intended to be within the spirit and scope of the present disclosure. Accordingly, the foregoing description and drawings are by way of example only.

The above-described embodiments of the present disclosure can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the concepts disclosed herein may be embodied as a non-transitory computer-readable medium (or multiple computer-readable media) (e.g., a computer memory, one or more floppy discs, compact discs, optical discs, magnetic tapes, flash memories, circuit configurations in Field Programmable Gate Arrays or other semiconductor devices, or other non-transitory, tangible computer storage medium) encoded with one or more programs that, when executed on one or more computers or other processors, perform methods that implement the various embodiments of the present disclosure discussed above. The computer-readable medium or media can be transportable, such that the program or programs stored thereon can be loaded onto one or more different computers or other processors to implement various aspects of the present disclosure as discussed above.

The terms "program" or "software" are used herein to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various features and aspects of the present disclosure may be used alone, in any combination of two or more, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the concepts disclosed herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc. in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

What is claimed is:

1. A clinical monitoring system comprising:
   one or more memory units each operable to store at least one program; and
   at least one processor communicatively coupled to the one or more memory units, in which the at least one program, when executed by the at least one processor, causes the at least one processor to perform the operations of:
      monitoring clinical data, the clinical data representative of one or more characteristics of a respective clinical trial site, multiple clinical trial sites, a geographic region, and one or more clinical subjects;
      generating one or more clinical data points for a control chart based on the clinical data;

applying a respective statistical process control (SPC) function to each of the clinical data to identify and distinguish non-random patterns from random patterns in the clinical data and generate a plurality of respective clinical data signals, wherein one of the respective clinical data signals is indicative of e-diary non-compliance, wherein one of the respective clinical data signals is indicative of study drug compliance, and wherein one of the respective clinical data signals is indicative of discordance between symptom scores;

applying, using a rules engine, one or more rules to each of the clinical data signal, and determining whether one or more of the clinical data signal meets clinical trial threshold alert criteria;

in response to determining that a respective clinical data signal meets clinical trial threshold alert criteria, wherein the clinical trial threshold alert criteria includes a criterion that is met when the SPC function identifies a non-random pattern in the clinical data:

updating a user interface at a client device to identify a corresponding one or more clinical trial sites and/or clinical subjects and to cause an intervention at the corresponding clinical trial sites and/or clinical subjects, wherein the user interface includes an e-diary non-compliance control chart indicative of e-diary non-compliance, wherein one or more clinical data points of the e-diary non-compliance control chart are updated based on the one of the respective SPC function clinical data signals indicative of e-diary non-compliance, wherein the user interface includes a study drug compliance control chart indicative of study drug compliance, wherein one or more clinical data points of the study drug compliance control chart are updated based on the one of the respective SPC function clinical data signals indicative of study drug compliance, wherein the user interface includes a discordance between symptom scores control chart indicative of discordance between symptom scores, wherein one or more clinical data points of the discordance between symptom scores control chart are updated based on the one of the respective SPC function clinical data signals indicative of discordance between symptom scores; and in response to determining that the respective clinical data signal does not meet clinical trial threshold alert criteria:

updating a user interface at a corresponding client device to visualize one or more representations of the clinical data signals.

2. The system of claim 1, wherein clinical trial threshold alert criteria is met when the one or more of the respective clinical data signal exceeds a respective clinical trial threshold.

3. The system of claim 2, wherein the processor is further configured to perform the operation of: adjusting the clinical trial threshold to minimize the number of false positive and false negatives.

4. The system of claim 1, wherein the processor is further configured to perform the operation of:

selecting one or more clinical data, from a set of clinical data signals based on whether the selected clinical data signal is a respective clinical data signal.

5. The system of claim 1, wherein the processor is further configured to: forego selecting clinical data, from a set of clinical data signals based on whether the selected clinical data signal is a static clinical data.

6. The system of claim 1, wherein statistical process control functions include at least one of: a regression analysis to assess a treatment difference between a placebo and an active drug involved in the clinical trial.

7. The system of claim 1, wherein further intervention includes at least one of: root cause analysis, subject retraining, subject exclusion, site retraining, and/or site exclusion.

8. The system of claim 1, wherein the clinical data is time-varying.

9. A clinical monitoring method comprising:

monitoring clinical data, the clinical data representative of one or more characteristics of a respective clinical trial site, multiple clinical trial sites, a geographic region, and one or more clinical subjects;

generating one or more clinical data points for a control chart based on the clinical data;

applying a respective statistical process control (SPC) function to each of the clinical data to identify and distinguish non-random patterns from random patterns in the clinical data and generate a plurality of respective clinical data signals, wherein one of the respective clinical data signals is indicative of e-diary non-compliance, wherein one of the respective clinical data signals is indicative of study drug compliance, and wherein one of the respective clinical data signals is indicative of discordance between symptom scores;

applying, using a rules engine, one or more rules to each of the clinical data signal, and determining whether one or more of the clinical data signal meets clinical trial threshold alert criteria;

in response to determining that a respective clinical data signal meets clinical trial threshold alert criteria, wherein the clinical trial threshold alert criteria includes a criterion that is met when the SPC function identifies a non-random pattern in the clinical data:

updating a user interface at a client device to identify a corresponding one or more clinical trial sites and/or clinical subjects and to cause an intervention at the corresponding clinical trial sites and/or clinical subjects, wherein the user interface includes an e-diary non-compliance control chart indicative of e-diary non-compliance, wherein one or more clinical data points of the e-diary non-compliance control chart are updated based on the one of the respective SPC function clinical data signals indicative of e-diary non-compliance, wherein the user interface includes a study drug compliance control chart indicative of study drug compliance, wherein one or more clinical data points of the study drug compliance control chart are updated based on the one of the respective SPC function clinical data signals indicative of study drug non-compliance, wherein the user interface includes a discordance between symptom scores control chart indicative of discordance between symptom scores, wherein one or more clinical data points of the discordance between symptom scores control chart are updated based on the one of the respective SPC function clinical data signals indicative of discordance between symptom scores; and in response to determining that the respective clinical data signal does not meet clinical trial threshold alert criteria:
	updating a user interface at a corresponding client device to visualize one or more representations of the clinical data signals.

10. The method of claim 9, wherein clinical trial threshold alert criteria is met when the one or more of the respective clinical data signal exceeds a respective clinical trial threshold.

11. The method of claim 10, further comprising: adjusting the clinical trial threshold to minimize the number of false positive and false negatives.

12. The method of claim 9, further comprising:
	selecting one or more clinical data, less than all, from a set of clinical data signals based on whether the selected clinical data signal is a respective clinical data signal.

13. The method of claim 9, further comprising: forego selecting clinical data, from a set of clinical data signals based on whether the selected clinical data signal is a static clinical data.

14. The method of claim 9, wherein statistical process control functions include at least one of: a regression analysis to assess a treatment difference between a placebo and an active drug involved in the clinical trial.

15. The method of claim 9, wherein intervening at the corresponding clinical trial sites and/or clinical subjects includes a root cause analysis, subject retraining, subject exclusion, site retraining, and/or site exclusion.

16. The method of claim 9, wherein the clinical data is time-varying.

\* \* \* \* \*